United States Patent
Hammonds et al.

(10) Patent No.: US 6,211,142 B1
(45) Date of Patent: *Apr. 3, 2001

(54) COMPOSITIONS COMPRISING GAS6 POLYPEPTIDES AND ARTICLES OF MANUFACTURE COMPRISING THE SAME

(75) Inventors: R. Glenn Hammonds, Berkeley; Paul J. Godowski; Melanie R. Mark, both of Burlingame, all of CA (US)

(73) Assignee: Genentech, Inc., So. San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/402,253

(22) Filed: Mar. 10, 1995

(51) Int. Cl.$^7$ .............................. A61K 38/17; C07K 14/47
(52) U.S. Cl. ................................ 514/2; 514/12; 530/300; 530/350; 930/10
(58) Field of Search .......................... 514/2, 12; 530/300, 530/350; 930/10; 436/69.1, 69.6, 71.1, 240.1, 243, 244, 252.3, 320.1; 536/23.1, 23.5

(56) References Cited

U.S. PATENT DOCUMENTS

| | | | | |
|---|---|---|---|---|
| 4,775,624 | * | 10/1988 | Bang et al. | 435/226 |
| 5,116,964 | * | 5/1992 | Capon et al. | 536/27 |
| 5,538,861 | * | 7/1996 | Schneider et al. | 435/69.1 |

OTHER PUBLICATIONS

Sinha et al. J. Biol Chem 268(5):3048–3051, 1993.*
Esmon et al. J. Biol. Chem. 258(9):5548–5553, 1983.*
Stratagene Catalog (1988, p. 39).*
Bellosta et al., "The Receptor Tyrosine Kinase ARK Mediates Cell Aggregation by Homophilic Binding" *Molecular & Cellular Biology* 15(2):614–625 (Feb. 1995).
Brummendorf et al., "Axonal Glycoproteins with Immunoglobulin– and Fibronectin Type III–Related Domains in Vertebrates: Structural Features, Binding Activities and Signal Transduction", *Journal of Neurochemistry* 61(4):1207–1219 (1993).
Colombo et al., "Localization of Growth arrest–specific genes on mouse Chromosomes 1, 7, 8, 11, 13, and 16" *Mammalian Genome* 2:130–134 (1992).
Dahlback et al., "High molecular weight complex in human plasma between vitamin K–dependent protein S and complement component C4b–binding protein" *Proc. Natl. Acad. Sci. USA* 78(4):2512–2516 (Apr. 1981).
Dai et al., "Molecular Cloning of a Novel Receptor Tyrosine Kinase, tif, Highly Expressed in Human Ovary and Testis" *Oncogene* 9:975–979 (1994).
Esmon, "The Protein C Anticoagulant Pathway" *Arteriosclerosis and Thrombosis* 12(2):135–145 (Feb. 1992).

Ferrero et al., "Expression of a Growth Arrest Specific Gene (gas–6) During Liver Regeneration: Molecular Mechanisms and Signalling Pathways" *Journal of Cellular Physiology* 158:263–269 (1994).
Fujimoto, "brt, A Mouse Gene Encoding a Novel Receptor–type Protein–Tyrosine Kinase, is Preferentially Expressed in the Brain" *Oncogene* 9:693–698 (1994).
Gasic et al., "Coagulation factros X, Xa, and protein S as potent mitogens of cultured aortic smooth muscle cells" *Proc. Natl. Acad. Sci. USA* 89:2317–2320 (Mar. 1992).
Graham et al., "Cloning and mRNA Expression Analysis of a Novel Human Protooncogene, c–mer[1]" *Cell Growth & Differentiation* 5:647–657 (Jun. 1994).
Griffin et al., "Reevaluation of Total, Free, and Bound Protein S and C4b–Binding Protein Levels in Plasma Anticoagulated With Citrate or Hirudin" *Blood* 79(12):3203–3211 (Jun. 1992).
Hammond et al., "The cDNA–deduced primary structure of human sex hormone–binding globulin and location of its steroid–binding domain" *FEBS Letters* 215(1):100–104 (May 1987).
Janssen et al., "A novel putative tyrosine kinase receptor with oncogenic potential" *Oncogene* 6:2113–2120 (1991).
Joseph et al., "Sex hormone–binding globulin, androgen–binding protein, and vitamin K–dependent protein S are homologous to laminin A, merosin, and Drosophila crumbs protein" *FASEB J.* 6:2477–2481 (1992).
Lai et al., "Structure, expression, and activity of Tyro 3, a neural adhesion–related receptor tyrosine kinase" *Oncogene* 9:2567–2578 (1994).
Manfioletti et al., "The protein encoded by a growth arrest–specific gene (gas6) is a new member of the vitamin K–dependent proteins related to protein S, a negative coregulator in the blood coagulation cascade" *Molecular & Cellular Biology* 13(8):4976–4985 (Aug. 1993).
Mark et al., "rse, a Novel Receptor–type Tyrosine Kinase with Homology to Ax1/Ufo, Is Expressed at High Levels in the Brain" *Journal of Biological Chemistry* 269(14):10720–10728 (Apr. 8, 1994).
O'Bryan et al., "axl, a transforming gene isolated from primary human myeloid leukemia cells, encodes a novel receptor tyrosine kinase" *Molecular & Cellular Biology* 11(10):5016–5031 (Oct. 1991).

(List continued on next page.)

*Primary Examiner*—Christine Saoud
(74) *Attorney, Agent, or Firm*—David A. Carpenter

(57) ABSTRACT

An activator of the Rse receptor protein tyrosine kinase has been identified which is encoded by growth arrest-specific gene 6 (gas6). Accordingly, the present invention provides compositions comprising gas6 polypeptides wherein the gas6 polypeptides are present in an amount effective for activating the Rse receptor. The present invention is further directed to articles of manufacture comprising gas6 polypeptides such as kits and containers containing gas6 polypeptide compositions and gas6 polypeptide In a liposome or adsorbed to a membrane.

31 Claims, 13 Drawing Sheets

OTHER PUBLICATIONS

Ohashi et al., "Cloning of the cDNA for a Novel Receptor Tyrosine Kinase, Sky, Predominantly Expressed in Brain" *Oncogene* 9:699–705 (1994).

Rescigno et al., "A putative receptor tyrosine kinase with unique structural topology" *Oncogene* 6:1909–1913 (1991).

Rutishauser, "Adhesion molecules of the nervous system" *Current Opinion in Neurobiology* 3:709–715 (1993).

Schneider et al., "Genes Specifically Expressed at Growth Arrest of Mammalian Cells" *Cell* 54:787–793 (Sep. 9, 1988).

Schulz et al., "Isolation and expression analysis of tyro3, a murine growth factor receptor tyrosine kinase preferentially expressed in adult brain" *Molecular Brain Research* 28:273–280 (1995).

Stitt et al., "The anticoagulation Factor Protein S and Its Relative, Gas6, are Ligands for the Tyro 3/Axl Family of Receptor Tyrosine Kinases" *Cell* 80:661–670 (Feb. 1995).

Varnum et al., "Axl receptor tyrosine kinase stimulated by the vitamin K–dependent protein encoded by growth–arrest–specific gene 6" *Nature* 373:623–626 (Feb. 1995).

Walker, "Regulation of Activated Protein C by Protein S" *Journal of Biological Chemistry* 256(21):11128–11131 (Nov. 1981).

Walker, "Regulation of Vitamin K–dependent Protein S" *Journal of Biological Chemistry* 259(16):10335–10339 (Aug. 1984).

Walker et al., "Inactivation of Factor VIII by Activated Protein C and Protein S" *Archives of Biochemistry & Biophysics* 252(1):322–328 (Jan. 1987).

Walker et al., "Regulation of Activated Protein C by a New Protein" *Journal of Biological Chemistry* 255(12):5521–5524 (Jun. 1980).

Biesecker et al., "Identification of Alternative Exons, Including a Novel Exon, in the Tyrosine Kinase Receptor Gene Etk2/tyro3 That Explain Differences in 5' cDNA Sequences" *Oncogene* 10:2239–2242 (1995).

Dahlback et al., "Primary Structure of Bovine Vitamin K–dependent Protein S" *Proc. Natl. Acad. Sci. USA* 83:4199–4203 (Jun. 1986).

Fridell et al., "Differential Activation of the Ras/Extracellular–Signal–Regulated Protein Kinase Pathway is Responsible for the Biological Consequences Induced by the axl receptor tyrosine kinase" *Molecular & Cellular Biology* 16(1):135–145 (Jan. 1996).

Godowski et al., "Reevaluation of the Roles of Protein S and Gas6 as Ligands for the Receptor Tyrosine Kinase Rse/Tyro3" *Cell* 82:355–358 (Aug. 11, 1995).

Li et al., "Identification of Gas6 as a Growth Factor for Human Schwann Cells" *The Journal of Neuroscience* 16(6):2012–2019 (Mar. 15, 1996).

Mark et al., "Characterization of Gas6, a Member of the Superfamily of G Domain–containing Proteins, as a Ligand for Rse and Axl" *The Journal of Biological Chemistry* 271(16):9785–9789 (Apr. 19, 1996).

Mark et al., "Expression and Characterization of Hepatocyte Growth Factor Receptor–IgG Fusion Proteins" *The Journal of Biological Chemistry* 267(36):26166–26171 (Dec. 25, 1992).

McCloskey et al., "Activation of the Axl Receptor Tyrosine Kinase Induces Mitogenesis and Transformation in 32D Cells" *Cell Growth and Differentiation* 5:1105–1117 (Oct. 1994).

Neubauer et al., "Expression of Axl, a Transforming Receptor Tyrosine Kinase, in Normal and Malignant Hematopoiesis" *Blood* 84(6):1931–1941 (Sep. 15, 1994).

Ohashi et al., "Stimulation of Sky Receptor Tyrosine Kinase by the Product of Growth Arrest–Specific Gene 6" *The Journal of Biological Chemistry* 270(39):22681–22684 (Sep. 29, 1995).

Taylor et al., "Mouse Mammary Tumors Express Elevated Levels of RNA Encoding the Murine Homolog of Sky, a Putative Receptor Tyrosine Kinase" *The Journal of Biological Chemistry* 270(12):6872–6880 (Mar. 24, 1995).

Nakano, Toru, et al., "Vascular Smooth Muscle Cell–derived, Gla–containing Growth–potentiating Factor for $Ca^{2+}$–mobilizing Growth Factors*", *The Journal of Biological Chemistry*, vol. 270(11):5702–5705 (Mar. 17, 1995).

Goruppi, Sandro, et al., "Gas6, the ligand of Axl tyrosine kinase receptor, has mitogenic and survival activities for serum starved NIH3T3 fibroblasts", *Oncogene*, 12:471–480 (1996).

* cited by examiner

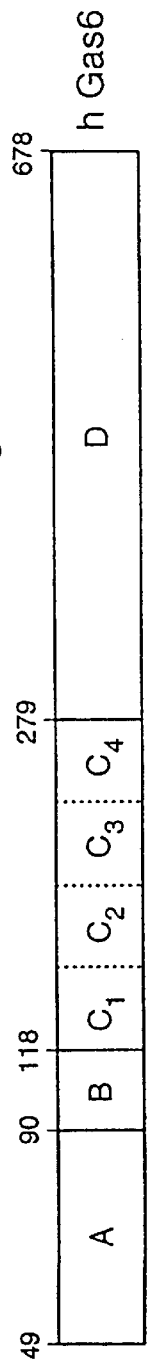
FIG. 1A
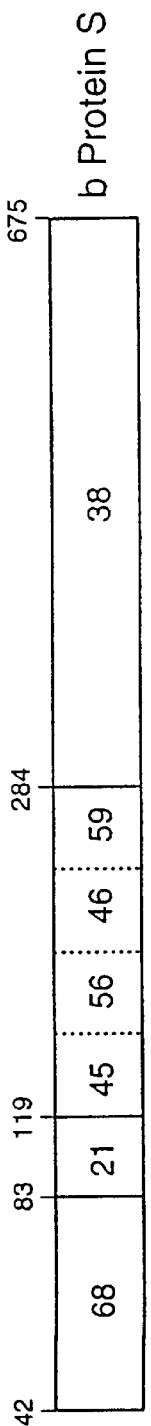
FIG. 1B
FIG. 1C
FIG. 1D

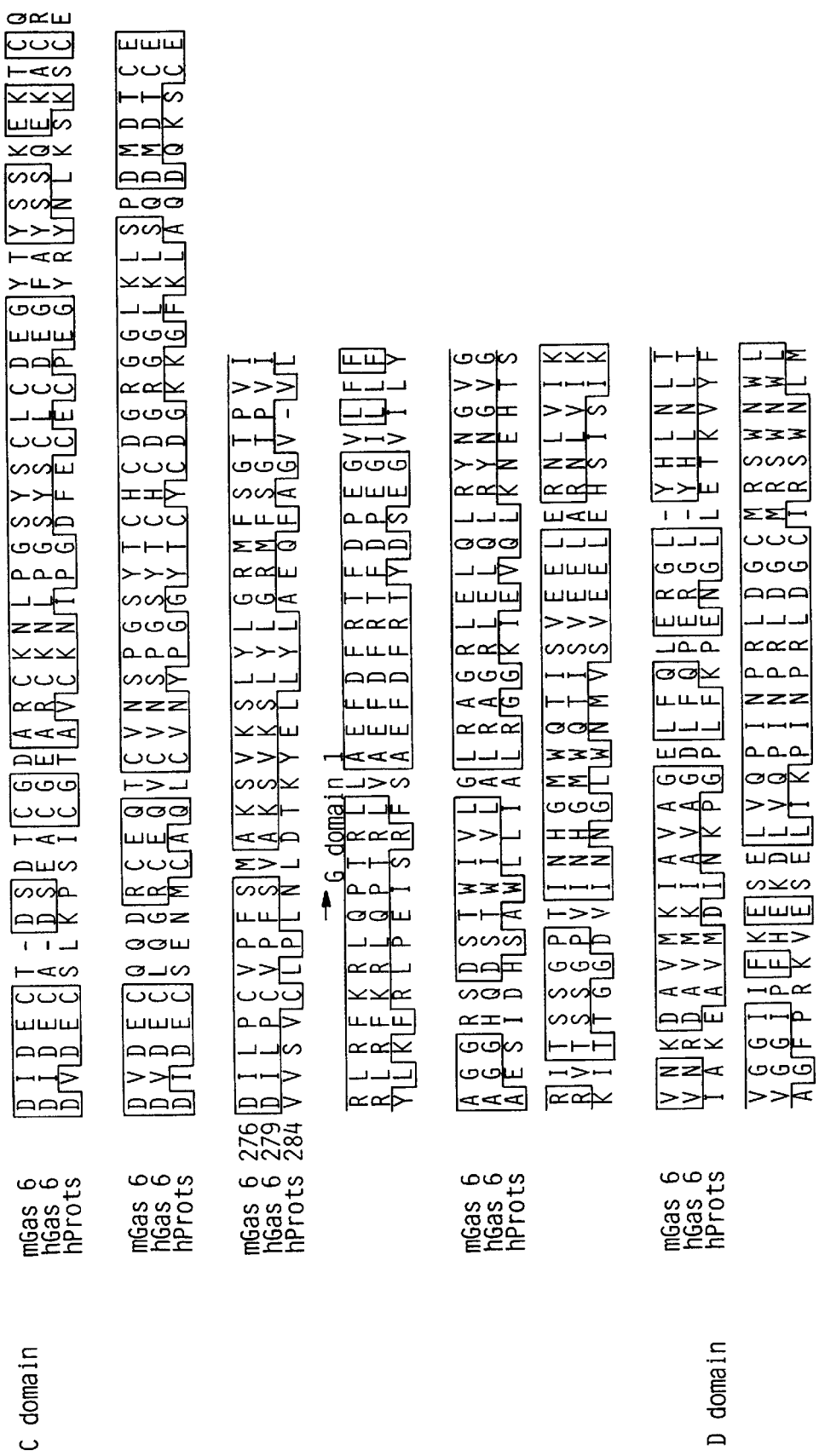

FIG. 2C

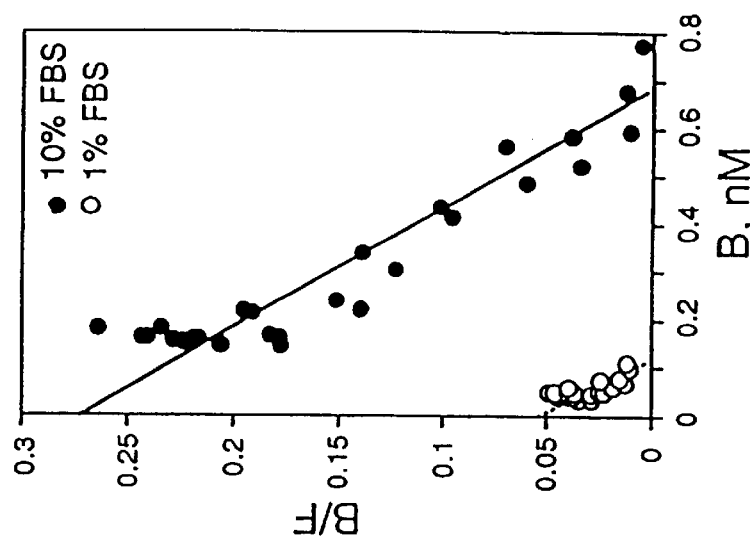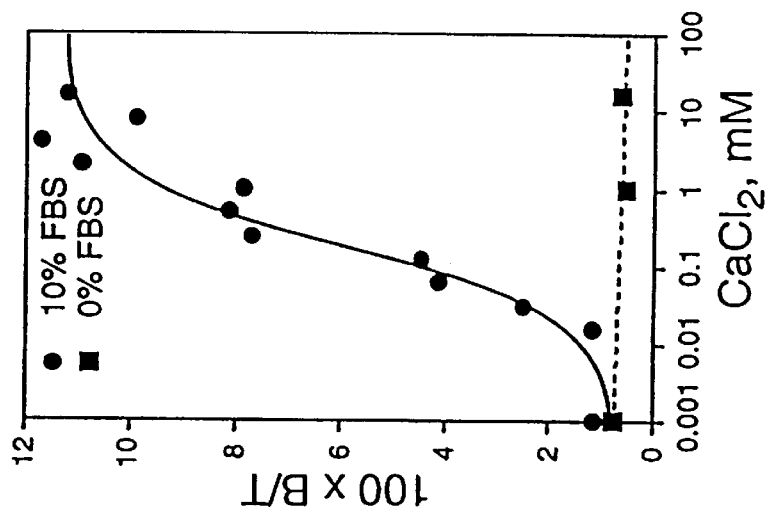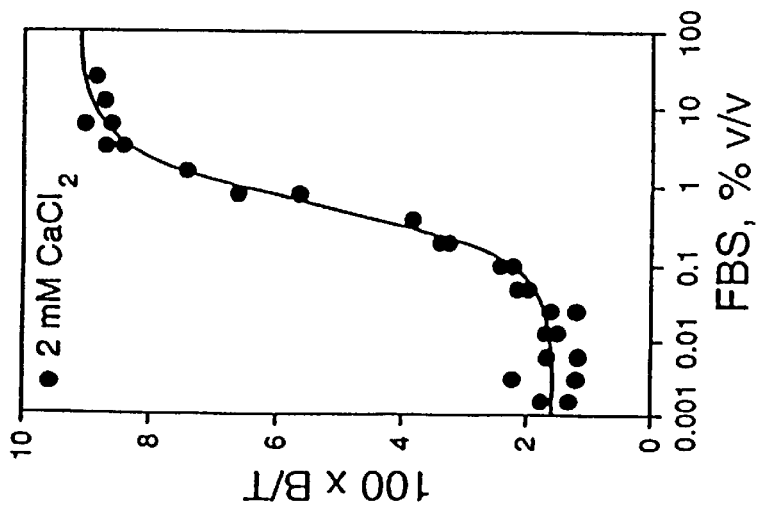

COMPOSITIONS COMPRISING GAS6 POLYPEPTIDES AND ARTICLES OF MANUFACTURE COMPRISING THE SAME

BACKGROUND OF THE INVENTION

1. Field of the Invention

The invention relates generally to methods of activating the Rse tyrosine kinase receptor. More particularly, the invention relates to methods of enhancing survival, proliferation and/or differentiation of cells comprising the Rse receptor (such as glial cells) using gas6. The invention also relates to gas6 variants, particularly those which are less γ-carboxylated than gas6 isolated from nature.

2. Description of Related Art

Specific signals that control the growth and differentiation of cells in developing and adult tissues often exert their effects by binding to and activating cell surface receptors containing an intrinsic tyrosine kinase activity. Mark et al. recently described the human and murine complementary DNA sequences of the receptor tyrosine kinase Rse that is preferentially expressed in the adult brain (Mark et al., *J. Biol. Chem.* 269:10720 [1994]). The extracellular domain of Rse receptor is composed of two immunoglobulin-like (Ig-L) repeats followed by two fibronectin type III repeats. Complementary DNA sequences encoding proteins identical to human (Ohashi et al., *Oncogene* 9:699 [1994]) and murine Rse (Lai et al, *Oncogene* 9:2567 [1994]) have been reported independently, and termed Sky and Tyro3, respectively. See also Fujmimoto and Yamamoto *Oncogene* 9: 693 (1994) concerning the murine equivalent to Rse they call brt and Dai et al. *Oncogene* 9: 975 (1994) with respect to the human molecule they call tif.

The expression of Rse in various tissues has been investigated. Lai et al., supra, found that, in the adult brain, Rse mRNA is localized in neurons of the neocortex, cerebellum and hippocampus. Schulz et al. similarly found that Rse is expressed at high levels in the cerebral cortex, the lateral septum, the hippocampus, the olfactory bulb and in the cerebellum. The highest levels of Rse expression in the brain were found to be associated with neurons. (Schulz et al. *Molec. Brain Res.* 28: 273–280 [1995]). In the central nervous system (CNS) of mice, the expression of Rse is detected at highest levels during late embryonic stages and post birth, coincident with the establishment and maintenance of synaptic circuitry in cortical and hippocampal neurons (Lai et al., supra and Schneider et al., *Cell* 54:787–793 [1988]). This process is believed to be regulated locally, by cells that are in direct contact or positioned close to one another. By Northern blot analysis, Mark et al., supra, found that high levels of Rse mRNA were present in samples of RNA from the brain and kidney. Dai et al., supra found that Rse was highly expressed in human ovary and testes. The expression of Rse in various human cell lines was also analyzed by Mark et al., supra. Little, or no, Rse mRNA was detected by Northern blotting of mRNA samples from the monocyte cell line THP-1 or the lymphoblast-like RAJI cells. However, the Rse transcript was detected in a number of hematopoietic cell lines, including cells of the myeloid (i.e., myelogenous leukemia line K562 and myelomonocytic U937 cells) and the megakaryocytic leukemia lines DAMI and CMK11-5, as well as the human breast carcinoma cell line MCF-7. In the cell lines examined, the highest level of expression was observed in Hep 3B cells, a human hepatocarcinoma cell line.

Rse is structurally related to Axl (also known as Ufo or Ark) and shares 43% overall amino acid sequence identity with this tyrosine kinase receptor. See O'Bryan et al., *Mol. Cell. Biol.* 11:5016 (1991), Janssen et al., *Oncogene* 6:2113 (1991), Rescigno et al. *Oncogene* 5:1908 (1991) and Bellosta et al. 15: 614 (1995) concerning Axl. Rse and Axl, together with c-Mer (Graham et al., *Cell Growth Differ.* 5:647 [1994]), define a class of receptor tyrosine kinases whose extracellular domains resemble neural cell recognition and adhesion molecules (reviewed by Ruitishauser, U. in *Current Opin. Neurobiology* 3:709 [1993] and Brummendorf and Rathjen in *J. Neurochemistry* 61:1207 [1993]). Like Rse, Axl is also expressed in the nervous system, but is more widely expressed than Rse in peripheral tissues.

Putative ligands for the Rse and Axl receptors have been reported. Varnum et al. *Nature* 373:623 (1995) and Stitt et al. *Cell* 80: 661–670(1995) recently reported that gas6 (for growth arrest-specific gene 6) is a ligand for Axl. Gas6 belongs to a set of murine genes which are highly expressed during serum starvation in NIH 3T3 cells (Schneider et al., *Cell* 54:787–793 [1988]). These genes were designated growth arrest-specific genes, since their expression is negatively regulated during growth induction. The human homolog of murine gas6 was also cloned and sequenced by Manfioletti et al. in *Molec. Cell Biol.* 13(8):4976–4985 (1993). They concluded that gas6 is a vitamin K-dependent protein and speculated that it may play a role in the regulation of a protease cascade relevant in growth regulation. Gas6 is expressed in a variety of tissues including the brain. See also Colombo et al. *Genome* 2:130–134 (1992) and Ferrero et al. *J. Cellular Physiol.* 158:263–269(1994) concerning gas6.

Stitt et al., supra further reported that protein S is the ligand for Tyro3. Protein S is a vitamin K-dependent plasma protein that functions as an anticoagulant by acting as a cofactor to stimulate the proteolytic inactivation of factors Va and VIIIa by activated protein C. Reviewed in Easmon et al. *Aterioscler. Thromb.* 12:135 (1992). Accordingly, protein S is an important negative regulator of the blood-clotting cascade. See Walker et al., *J. Biol. Chem.* 255:5521–5524 (1980), Walker et al., *J. Biol. Chem.* 256:11128–11131 (1981), Walker et al., *Arch. Biochem. Biophys.* 252: 322–328 (1991), Griffin et al. *Blood* 79: 3203 (1992) and Easmon, D., *Aterioscler. Thromb.* 12:135 (1992). The discovery that about half of the protein S in human plasma is bound to C4BP further supports the notion that protein S is involved in the complement cascade. Dahlback et al., *PNAS(U.S.A.)* 78: 2512–2516(1981). The role of protein S as a mitogen for smooth muscle cells has also been reported. Gasic et al., *PNAS (U.S.A.)* 89:2317–2320(1992).

Protein S can be divided into four domains (see FIGS. 1A, 1C and 1D herein). Residues 1–52 (Region A) are rich in γ-carboxyglutamic acid (Gla) residues which mediate the $Ca^{2+}$ dependent binding of protein S to negatively charged phospholipids (Walker, *J. Biol. Chem.* 259:10335 [1984]). Region B includes a thrombin-sensitive loop. Region C contains four epidermal growth factor (EGF)-like repeats. Region D is homologous to the steroid hormone binding globulin (SHBG) protein (Hammond et al., *FEBS Lett.* 215:100 [1987]). As discussed by Joseph and Baker (*FASEB J.* 6:2477 [1994]), this region is homologous to domains in the A chain of laminin (23% identity) and merosin (22% identity) and to a domain in the Drosophila crumbs (19%).

Murine and human gas6 cDNAs encode proteins having 43 and 44% amino acid sequence identity respectively to human protein S.

SUMMARY OF THE INVENTION

The foregoing invention relates to gas6 variants which are essentially not γ carboxylated or are substantially less γ carboxylated than gas6 derived from an endogenous source of the molecule. Examples of such variants include gas6 variants lacking one or more glutamic acid residues from the A domain of gas6 which are normally γ carboxylated, fragments of gas6 which lack the A domain as well as fragments which consist essentially of the D domain of gas6 (or a G domain fragment of gas6).

The invention provides a method of activating the Rse receptor by exposing a cell (preferably a human cell) comprising the Rse receptor to exogenous gas6 in an amount effective to activate the Rse receptor. The Rse receptor is normally cell-bound and the gas6 is preferably human gas6. The invention also provides a method of enhancing survival, proliferation and/or differentiation of a cell which has the Rse receptor incorporated in the cell membrane thereof by exposing the cell to gas6 in an amount effective to enhance survival, proliferation and/or differentiation of the cell. The cell is often a neuron or a glial cell, such as a Schwann cell. The cell may be present in cell culture or in a mammal (e.g. a human) which is suffering from a neurologic disease or disorder. Often, the gas6 is provided in a physiologically acceptable carrier.

The invention also provides kits and articles of manufacture comprising gas6 polypeptide. The article of manufacture usually comprises instructions for using the gas6 in an in vitro cell culture or for administering the gas6 to a mammal.

BRIEF DESCRIPTION OF THE DRAWINGS

FIGS. 1A–1D provide a schematic representation of the structure of protein S and gas6 (FIG. 1A) and comparison of the amino acid homology between the bovine (b) and human (h) forms of protein S (FIGS. 1C and 1D, respectively) with human gas6 (FIG. 1B). For h gas6, boxes represent the Gla region (i.e. the A domain), the loop region (i.e. the B domain), the 4 EGF-like repeats (labeled $C_1$–$C_4$) which form the C domain, and the region homologous to sex-hormone binding globulin (i.e. the D domain), which is also related to the G domains of laminin A chain and merosin and to Drosphilia crumbs protein. The percentage of amino acid identity shared between h gas6 and either b protein S or h protein S is indicated within the corresponding boxes. The amino acids at the boundaries of each of the regions are indicated above the boxes.

FIGS. 3A–3D are graphs depicting characterization of the Rse-L in fetal bovine serum (FBS). FIG. 3A shows binding of $^{125}$I-Rse-IgG as a function of FBS concentration. Binding, percent of total counts added that are membrane associated (100×B/T, i.e. bound/total), is plotted as a function of FBS concentration. The data were fit to a 4 parameter model which gave an $EC_{50}$ of 0.58% v/v. FIG. 3B illustrates binding of $^{125}$I-Rse-IgG as a function of $Ca^{2+}$ concentration, with constant FBS concentration. Binding was performed as in FIG. 3A either in the presence of 10% diafiltered FBS or in its absence and varying the concentration of added $Ca^{2+}$. The $EC_{50}$ of $Ca^{2+}$ as judged by a 4 parameter fit to the data is 0.18 mM. FIG. 3C is a Scatchard analysis of $^{125}$I-Rse-IgG binding to CMK11-5 membranes mediated by FBS. A single concentration of $^{125}$I-Rse-IgG, FBS and $Ca^{2+}$ was used with increasing concentrations of unlabeled Rse-IgG, and binding plotted vs the ratio of bound and free (B/F) after correction for nonspecific binding. Experiments at both 1% ($K_d$=0.82 nM) and 10% ($K_d$=2.2 nM) FBS are shown. FIG. 3D is a KIRA analysis of dose dependent activation of Rse phosphorylation by the Q-sepharose enriched (QSE) fraction of FBS. The inset shows Rse-L activity was specifically neutralized by incubation with Rse-IgG. Rse phosphorylation is shown in serum starved cells (–); or cells treated with QSE fraction in the absence of added IgG proteins (QSE); or with QSE incubated with Rse-IgG or CD4-IgG as indicated.

In FIG. 6A binding of $^{125}$I-Rse-IgG to CMK11-5 membranes was enabled by addition of astrocyte conditioned medium (ACM), with a half maximum effect achieved at 13% v/v ACM. FIG. 6B is a KIRA analysis of phosphorylation of Rse by ACM. FIG. 6C shows that the phosphorylation of Rse by ACM was inhibited by incubation with Rse-IgG, but not CD4-IgG. Neutralization was carried out as described in FIG. 3 legend.

DETAILED DESCRIPTION OF THE PREFERRED EMBODIMENTS

1. Definitions

As used herein, the terms "gas6" and "gas6 polypeptide" (unless indicated otherwise) refer to a polypeptide which is able to activate the Rse receptor and encompass the mature, pre-, prepro- and pro- forms of gas6 polypeptide, either purified from a natural source, chemically synthesized or recombinantly produced. The present definition specifically includes "human" gas6 polypeptide comprising the amino acid sequence published in Manfioletti et al., *Mol. Cell. Biol.* 13(8):4976–4985 (1993) (available from EMBL/GenBank/DDBJ under accession number X59846) and other mammalian gas6 polypeptides (such as murine gas6, see Manfioletti et al., supra). Where the gas6 polypeptide has the amino acid sequence of a gas6 polypeptide found in nature, it is referred to herein as a "native" or "native sequence" polypeptide regardless of the method by which it is produced (e.g. it can be isolated from an endogenous source of the molecule or produced by synthetic techniques).

Figure 2A:
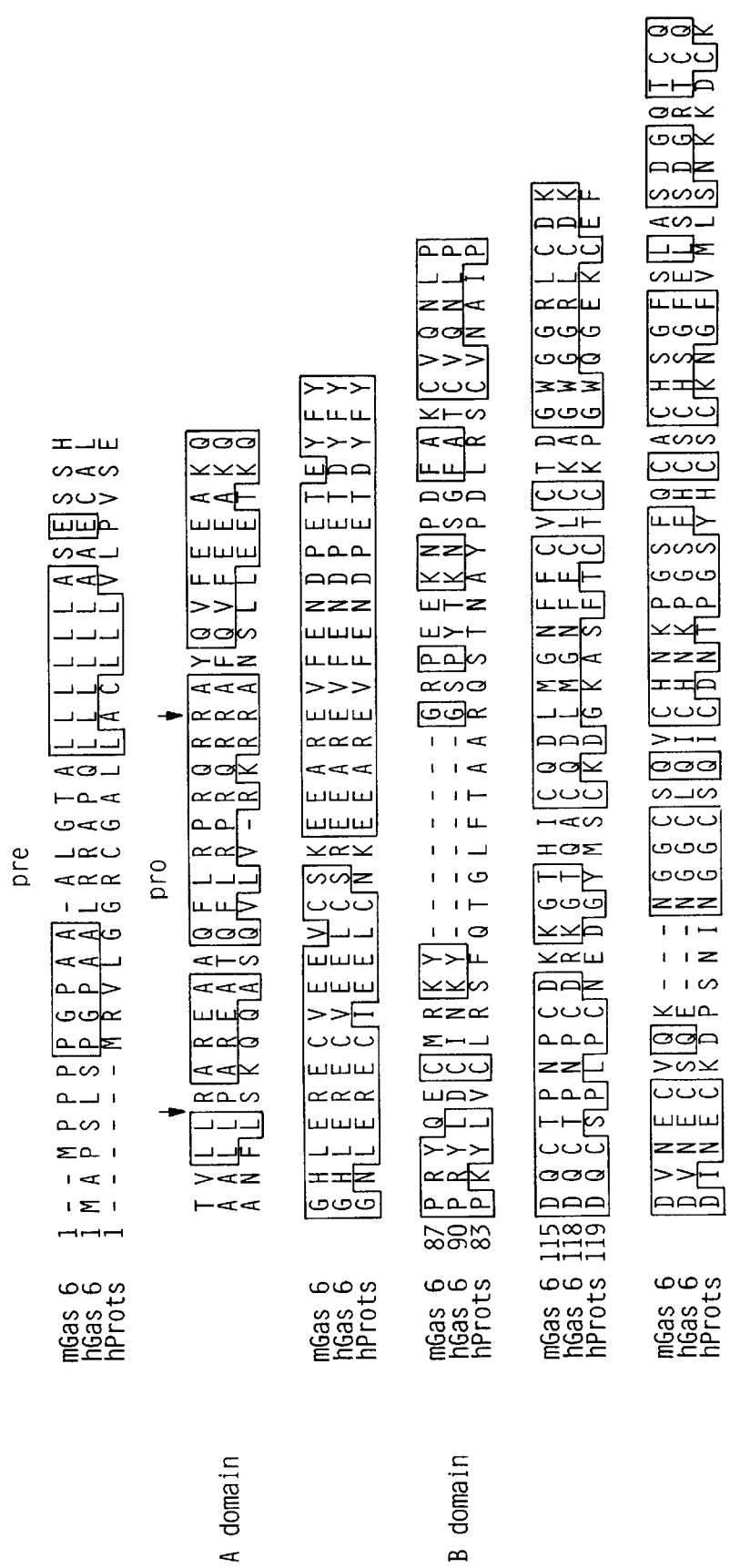
FIG. 2 shows a comparison of the amino acid sequences of murine gas6 (m gas6) [SEQ ID NO:1], h gas6 [SEQ ID NO:2] and h protein S [SEQ ID NO: 3]. Residues of the "pre" and "pro" sequences are indicated (with the arrow indicating the last residue of each precursor sequence). The A–D domains are delineated, as are the two G domains which reside in the D domain (i.e. G domain 1 and G domain 2).
Figure 2C:
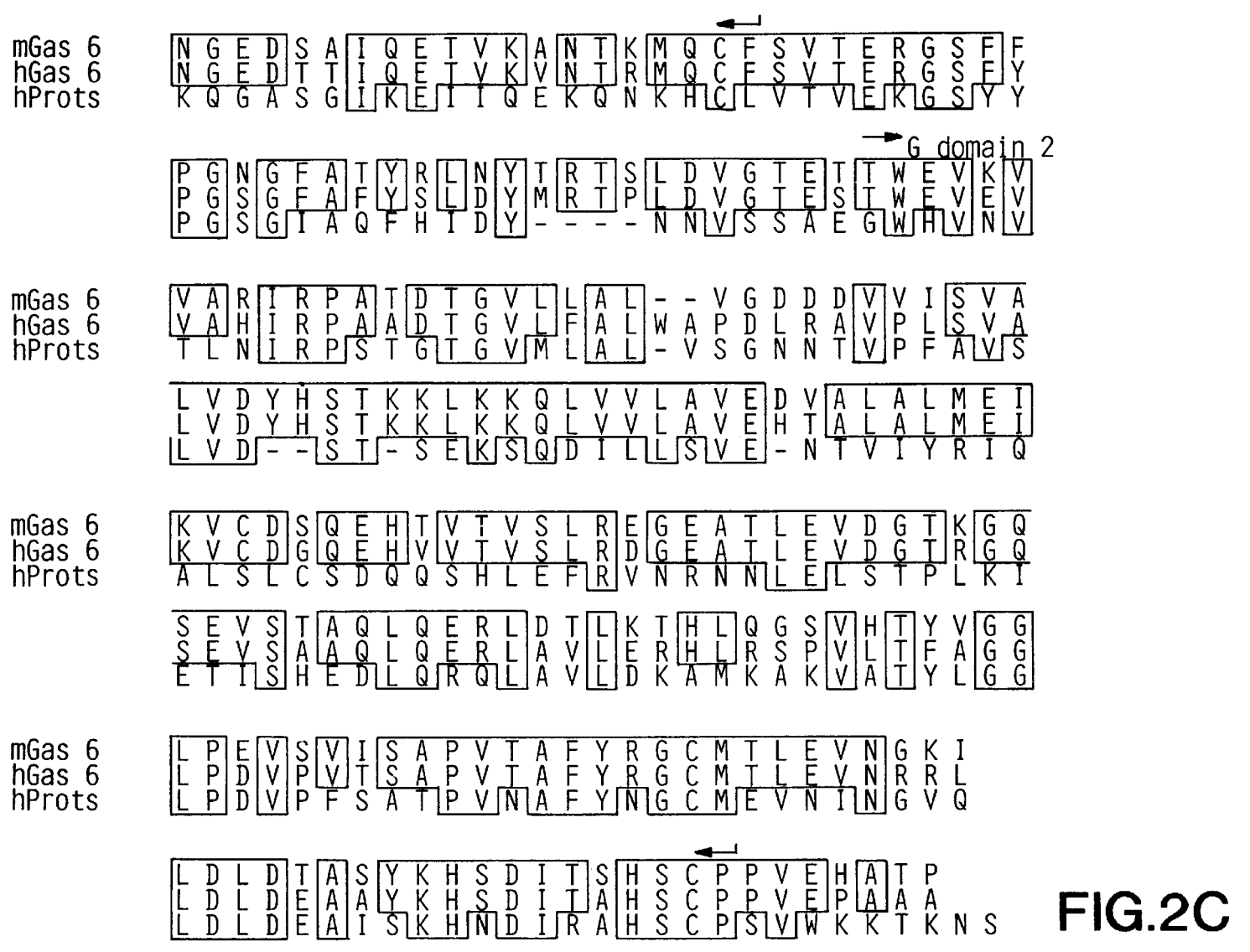

Gas6 has various amino acid "regions" or "domains" which are delineated in FIGS. 1A–B and FIG. 2. The "A domain" or "Gla region" at the amino terminus of the polypeptide has residues which are rich in γ-carboxyglutamic acid (Gla residues) which appear to mediate calcium dependent binding of gas6 to negatively charged phospholipids in cell membranes. The A-domain stretches from about residue 46–86 of murine gas6 and about residue 49–89 of human gas6. The following "B domain" comprises a thrombin sensitive "loop" and extends from about residue 87–114 of murine gas6 and about residue 90–117 of human gas6. The third domain called the "C domain" herein has four epidermal growth factor (EGF)-like repeats ($C_1$–$C_4$ in FIG. 1B). This C domain extends from about residue 115–275 of murine gas6 and about residue 118–278 of human gas6. The remaining "D domain" is homologous to steroid hormone binding globulin (SHBG) protein and comprises about residues 276–673 of murine gas6 and residues 279–678 of human gas6. The D domain comprises a pair of "G domains" called "G Domain 1" (i.e. about residues 311–468 for murine gas6 and about residues 314–471 for human gas6) and "G Domain 2" (i.e. about residues 500–666 for murine gas6 and about residues 503–671 for human gas6).

The terms "gas6" and "gas6 polypeptide" also encompass "variants" or "mutants" of native gas6. Such variants include fragments of the human gas6 sequence; polypeptides wherein one or more amino acid residues are added at the N- or C-terminus of, or within, the human gas6 sequence; one or more amino acid residues are deleted, and optionally substituted by one or more amino acid residues; and derivatives of the above proteins, polypeptides, or fragments thereof, wherein an amino acid residue has been covalently modified so that the resulting product is a non-naturally occurring amino acid. Gas6 variants may be made synthetically, for example, by site-directed or PCR mutagenesis, or may exist naturally, as in the case of allelic forms and other naturally occurring variants of the translated amino acid sequence set forth in Manfioletti et at. that may occur in human and other animal species.

A gas6 variant is included within the scope of the invention provided that it is functionally active. As used herein, "functionally active" and "functional activity" in reference to gas6 means that the gas6 is able to activate the Rse receptor and/or promote the proliferation, survival, and/or differentiation of cells comprising the Rse receptor such as neurons or glial cells. A "glial cell" is derived from the central and peripheral nervous system and can be selected from oligodendroglial, astrocyte, ependymal, or microglial cells as well as satellite cells of ganglia and the neurolemmal or Schwann cells around peripheral nerve fibers.

Often gas6 variants will share at least about 75% (preferably greater than 80% and more preferably greater than 90%) sequence identity with the translated amino acid sequence encoding mature gas6 or fragments thereof after aligning the sequences to provide for maximum homology, as determined, for example, by the Fitch et al., *PNAS (U.S.A.)* 80: 1382–1386 (1983), version of the algorithm described by Needleman et al., *J. Mol. Biol.* 48:443–453 (1970). In order to screen for functionally active gas6 variants, a variant can be subjected to one or more of the following functional activity tests/assays:

(a) Receptor activation assays which measure downregulation or activation of receptor tyrosine kinase activity (e.g. western blotting using an anti-phosphotyrosine antibody to determine whether the variant is able to activate Rse receptor, see Example 3 herein).

(b) KIRA ELISA to determine Rse receptor activation-capability of the variant as described in Example 4 below.

(c) Schwann cell proliferation assay to establish whether or not the variant is able to enhance Schwann cell proliferation in cell culture. See Example 9 herein.

Amino acid sequence variants of gas6 can be prepared by introducing appropriate nucleotide changes into gas6 DNA and thereafter expressing the resulting modified DNA in a host cell, or by in vitro synthesis. Such variants include, for example, deletions from, or insertions or substitutions of, amino acid residues within the gas6 amino acid sequence set forth in Manfioletti et al. Any combination of deletion, insertion, and substitution may be made to arrive at an amino acid sequence variant of gas6, provided that such variant possesses the desired characteristics described herein. Changes that are made in the amino acid sequence to arrive at an amino acid sequence variant of gas6 may also result in further modifications of gas6 upon its expression in host cells, for example, by virtue of such changes introducing or moving sites of glycosylation.

There are two principal variables in the construction of amino acid sequence variants of gas6: the location of the mutation site and the nature of the mutation. These are variants from the human gas6 amino acid sequence, and may represent naturally occurring allelic forms of gas6, or predetermined mutant forms of gas6 made by mutating gas6 DNA, either to arrive at an allele or a variant not found in nature. In general, the location and nature of the mutation chosen will depend upon the gas6 characteristic to be modified.

For example, due to the degeneracy of nucleotide coding sequences, mutations can be made in the human gas6 nucleotide sequence without affecting the amino acid sequence of the gas6 encoded thereby. Other mutations can be made that will result in a gas6 that has an amino acid sequence different from that set forth in Manfiolleti et al., but which is functionally active. Such functionally active amino acid sequence variants of gas6 are selected, for example, by substituting one or more amino acid residues in the human gas6 amino acid sequence with other amino acid residues of a similar or different polarity or charge.

One useful approach is called "alanine scanning mutagenesis". Here, an amino acid residue or group of target residues is/are identified (e.g., charged residues such as arg, asp, his, lys, and glu) and, by means of recombinant DNA technology, replaced by a neutral or negatively charged amino acid (most preferably alanine or polyalanine) to affect the interaction of the amino acids with the surrounding aqueous environment in or outside the cell. Cunningham et al., *Science* 244:1081–1085 (1989). Those domains demonstrating functional sensitivity to the substitutions are then refined by introducing further or other variants at or for the sites of substitution.

Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed gas6 variants are screened for functional activity as discussed above.

Amino acid sequence deletions generally range from about 1 to 30 residues, more preferably about 1 to 10 residues, and typically are contiguous. Deletions from regions of substantial homology with other tyrosine kinase receptor ligands, for example, are more likely to affect the functional activity of gas6. Generally, the number of consecutive deletions will be selected so as to preserve the tertiary structure of gas6 in the affected domain, e.g., β-pleated sheet or α helix. Preferred deletion mutants include those which lack one or more glutamic acid residues in the A domain of gas6 (i.e. those E residues in the A domain of gas6 shown in FIG. 2) or lack the A domain entirely. A preferred deletion mutant of gas6 is the D domain of gas6 or one of the G domains thereof.

Amino acid sequence insertions include amino- and/or carboxyl-terminal fusions ranging in length from one amino acid residue to polypeptides containing a hundred or more residues, as well as intrasequence insertions of single or multiple amino acid residues. Intrasequence insertions (i.e., insertions made within the human gas6 amino acid sequence) may range generally from about 1 to 10 residues, more preferably 1 to 5, most preferably 1 to 3. Examples of terminal insertions include gas6 with an N-terminal methionyl residue (such as may result from the direct expression of gas6 in recombinant cell culture), and gas6 with a heterologous N-terminal signal sequence to improve the secretion of gas6 from recombinant host cells. Other insertions include the fusion to the N- or C-terminus of gas6 of immunogenic polypeptides (for example, bacterial polypeptides such as β-lactamase or an enzyme encoded by the *E. coli* trp locus, or yeast protein), and C-terminal fusions with proteins having a long half-life such as immunoglobulin constant regions, albumin, or ferritin, as described in PCT Pub. No. WO 89/02922 (published Apr. 6, 1989).

The third group of variants are those in which at least one amino acid residue in the gas6 amino acid sequence, and preferably only one, has been removed and a different residue inserted in its place. The sites of greatest interest for making such substitutions are in the regions of the gas6 amino acid sequence that have the greatest homology with other tyrosine kinase receptor ligands. Those sites are likely to be important to the functional activity of the gas6. Accordingly, to retain functional activity, those sites, especially those falling within a sequence of at least three other identically conserved sites, are substituted in a relatively conservative manner. Such conservative substitutions are shown in Table 1 under the heading of "Preferred Substitution". If such substitutions do not result in a change in functional activity, then more substantial changes, denominated "Exemplary Substitutions" in Table 1, or as further described below in reference to amino acid classes, may be introduced and the resulting variant gas6 analyzed for functional activity.

TABLE 1

| Original Residue | Exemplary Substitutions | Preferred Substitution |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | ala; pro | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Insertional, deletional, and substitutional changes in the gas6 amino acid sequence may be made to improve the stability of gas6. For example, trypsin or other protease cleavage sites are identified by inspection of the encoded amino acid sequence for an arginyl or lysinyl residue. These are rendered inactive to protease by substituting the residue with another residue, preferably a basic residue such as glutamine or a hydrophobic residue such as serine; by deleting the residue; or by inserting a prolyl residue immediately after the residue. Also, any cysteine residues not involved in maintaining the proper conformation of gas6 for functional activity may be substituted, generally with serine, to improve the oxidative stability of the molecule and prevent aberrant crosslinking.

DNA encoding amino acid sequence variants of gas6 is prepared by a variety of methods known in the art. These methods include, but are not limited to, isolation from a natural source (in the case of naturally occurring amino acid sequence variants of gas6) or preparation by site-directed (or oligonucleotide-mediated) mutagenesis, PCR mutagenesis, and cassette mutagenesis of an earlier prepared DNA encoding a variant or a non-variant form of gas6.

Site-directed mutagenesis is a preferred method for preparing substitution, deletion, and insertion variants of gas6 DNA. This technique is well known in the art (see, e.g., Zoller et al., *Meth. Enz.* 100:4668–500 [1983]; Zoller et al., Meth. Enz. 154:329–350 [1987]; Carter, Meth. Enz. 154:382–403 [1987]; and Horwitz et al., Meth. Enz. 185:599–611 [1990]), and has been used, for example, to produce amino acid sequence variants of trypsin and T4 lysozyme, which variants have certain desired functional properties. Perry et al., Science 226:555–557 (1984); and Craik et al., Science 228:291–297 (1985).

Briefly, in carrying out site-directed mutagenesis of gas6 DNA, the gas6 DNA is altered by first hybridizing an oligonucleotide encoding the desired mutation to a single strand of such gas6 DNA. After hybridization, a DNA polymerase is used to synthesize an entire second strand, using the hybridized oligonucleotide as a primer, and using the single strand of gas6 DNA as a template. Thus, the oligonucleotide encoding the desired mutation is incorporated in the resulting double-stranded DNA.

PCR mutagenesis is also suitable for making amino acid sequence variants of gas6. See Higuchi, in *PCR Protocols*, pp.177–183 (Academic Press, 1990); and Vallette et al., *Nuc. Acids Res.* 17:723–733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., *Gene* 34:315–323(1985). The starting material is the plasmid (or other vector) comprising the gas6 DNA to be mutated. The codon(s) in the gas6 DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the gas6 DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated gas6 DNA sequence.

Covalent modifications of gas6 molecules also are included within the scope of this invention. For example, covalent modifications are introduced into gas6 by reacting targeted amino acid residues of the gas6 with an organic derivatizing agent that is capable of reacting with selected amino acid side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking gas6 to a water-insoluble support matrix or surface for diagnostic and/or therapeutic use. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group. Creighton, *Proteins: Structure and Molecular Properties*, pp.79–86 (W. H. Freeman & Co., 1983). Gas6 also is covalently linked to nonproteinaceous polymers, e.g. polyethylene glycol, polypropylene glycol or polyoxyalkylenes, in the manner set forth in U.S. Pat. Nos. 4,179,337; 4,301,144; 4,496,689; 4,640,835; 4,670,417; or 4,791,192.

The preferred gas6 is one which is "non-immunogenic in a human" which means that upon contacting the polypeptide in a pharmaceutically acceptable carrier and in a therapeutically effective amount with the appropriate tissue of a human, no state of sensitivity or resistance to the polypeptide is demonstrable upon the second administration of the polypeptide after an appropriate latent period (e.g., 8 to 14 days).

A preferred gas6 variant is one which is essentially not "γ carboxylated" or is less carboxylated than "native" gas6 derived from an endogenous source of the molecule (e.g. serum) or native gas6 made by a recombinant cell wherein the conditions for culturing such a cell facilitate γ carboxylation of the gas6 (e.g. Vitamin K is present in the culture media). Vitamin K is a cofactor for the carboxylase enzyme. The A domain of native gas6 has several glutamic acid residues which are normally γ carboxylated (see Manfioletti et al., supra). Accordingly, a convenient way to make a non-γ-carboxylated variant gas6 is to generate gas6 variants which lack one or more of the E residues from the A domain of native gas6 (see FIG. 2) or other gas6 fragments which lack this domain. The extent of γ carboxylation can be measured by amino acid sequence analysis or the barium chloride assay described in Example 11.

"gas6 antagonist" or "antagonist" refers to a substance that opposes or interferes with a functional activity of gas6. Examples of gas6 antagonists include neutralizing antibodies, Rse-IgG and Rse extracellular domain (Rse ECD).

The term "antibody" is used in the broadest sense and specifically covers single anti-gas6 monoclonal antibodies (including agonist and antagonist antibodies) and anti-gas6 antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-gas6 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g. U.S. Pat. No. 4,816,567 and Mage & Lamoyi, in *Monoclonal Antibody Production Techniques and Applications,* pp.79–97 (Marcel Dekker, Inc., New York [1987]).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods (U.S. Pat. No. 4,816,567). The "monoclonal antibodies" may also be isolated from phage libraries generated using the techniques described in McCafferty et al., *Nature* 348:552–554(1990), for example.

"Humanized" forms of non-human (e.g. murine) antibodies are specific chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

The term "neutralizing antibody" as used herein refers to an antibody that is capable of specifically binding to gas6, and which is capable of substantially inhibiting or eliminating the functional activity of gas6 in vivo and/or in vitro. Typically a neutralizing antibody will inhibit the functional activity of gas6 at least about 50%, and preferably greater than 80%, as determined, for example, by KIRA ELISA (see Example 4 below).

Polyclonal antibodies directed toward gas6 generally are raised in animals by multiple subcutaneous or intraperitoneal injections of gas6 and an adjuvant. It may be useful to conjugate gas6 or a peptide fragment thereof to a carrier protein that is immunogenic in the species to be immunized, such as keyhole limpet hemocyanin, serum albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (conjugation through lysine residues), glutaraldehyde, succinic anhydride, $SOCl_2$, or $R^1N=C=NR$, where R and $R^1$ are different alkyl groups.

Animals are immunized with such gas6-carrier protein conjugates combining 1 mg or 1 μg of conjugate (for rabbits or mice, respectively) with 3 volumes of Freund's complete adjuvant and injecting the solution intradermally at multiple sites. One month later the animals are boosted with ⅕th to ⅒th the original amount of conjugate in Freund's complete adjuvant by subcutaneous injection at multiple sites. Seven to 14 days later animals are bled and the serum is assayed for anti-gas6 antibody titer. Animals are boosted until the antibody titer plateaus. Preferably, the animal is boosted by injection with a conjugate of the same gas6 with a different carrier protein and/or through a different cross-linking agent. Conjugates of gas6 and a suitable carrier protein also can be made in recombinant cell culture as fusion proteins. Also, aggregating agents such as alum are used to enhance the immune response.

Monoclonal antibodies directed toward gas6 are produced using any method which provides for the production of antibody molecules by continuous cell lines in culture. Examples of suitable methods for preparing monoclonal antibodies include the original hybridoma method of Kohler et al., *Nature* 256:495–497 (1975), and the human B-cell hybridoma method, Kozbor, J., *Immunol.* 133:3001 (1984); Brodeur et al., *Monoclonal Antibody Production Techniques and Applications*, pp.51–63 (Marcel Dekker, Inc., New York, 1987).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be performed following methods known in the art (Jones et al., *Nature* 321:522–525 [1986]; Riechmann et al., *Nature* 332:323–327 [1988]; and Verhoeyen et al., *Science* 239:1534–1536 [1988]), by substituting rodent complementarity-determining regions (CDRs) for the corresponding regions of a human antibody.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, for example, Jakobovits et al., *PNAS* 90:2551–2555 (1993); Jakobovits et al., *Nature* 362:255–258 (1993); and Bruggermann et al., *Year in Immuno.* 7:33 (1993). Human antibodies can also be produced in phage-display libraries. Hoogenboom et al., *J. Mol. Biol.* 227:381 (1991); and Marks et al., *J. Mol. Biol.* 222:581 (1991).

The term "immunoadhesin" is used interchangeably with the expressions "gas6-immunoglobulin chimera" ("gas6-Ig") and "Rse-immunoglobulin chimera" ("Rse-Ig") and refers to a chimeric molecule that combines a functionally active gas6 (e.g. the D domain thereof) or Rse (e.g. the ECD thereof) with an immunoglobulin sequence. The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$.

Chimeras constructed from a protein sequence (e.g. Rse receptor ECD) linked to an appropriate immunoglobulin constant domain sequence (immunoadhesins) are known in the art. Immunoadhesins reported in the literature include fusions of the T cell receptor (Gascoigne et al., *PNAS (U.S.A.)* 84:2936–2940[1987]); CD4 (Capon et al., *Nature* 337:525–531 [1989]; Traunecker et al., *Nature* 339:68–70 [1989]; Zettmeissl et al., *DNA Cell Biol. U.S.A.* 9:347–353 [1990]; and Byrn et al., *Nature* 344:667–670 [1990]); L-selectin (Watson et al., *J. Cell. Biol.* 110:2221–2229 [1990]; and Watson et al., *Nature* 349:164–167[1991]); CD44 (Aruffo et al., *Cell* 61:1303–1313 [1990]); CD28 and B7 (Linsley et al., *J. Exp. Med.* 173:721–730 [1991]); CTLA-4 (Lisley et al., *J. Exp. Med.* 174:561–569[1991]); CD22 (Stamenkovic et al., *Cell* 66:1133–1144 [1991]; and TNF receptor (Ashkenazi et al., *PNAS (U.S.A.)* 88:10535–10539 [1991]).

The simplest and most straightforward immunoadhesin design combines the functionally active region(s) of the "adhesin" protein with the hinge and Fc regions of an immunoglobulin heavy chain. Ordinarily, when preparing the gas6- or Rse-immunoglobulin chimeras of the present invention, nucleic acid encoding the extracellular domain of Rse receptor or encoding gas6 (or a fragment thereof) will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain.

The precise site at which the fusion is made is not critical; particular sites are well known and may be selected in order to optimize the biological activity, secretion, or binding characteristics of the Rse- or gas6-immunoglobulin chimeras.

In some embodiments, the Rse- or gas6-immunoglobulin chimeras are assembled as monomers, or hetero- or homo-multimers, and particularly as dimers or tetramers, essentially as illustrated in WO 91/08298.

In a preferred embodiment, the gas6 sequence or Rse receptor extracellular domain sequence is fused to the N-terminus of the Fc domain of immunoglobulin $G_1$ ($IgG_1$). It is possible to fuse the entire heavy chain constant region to the gas6 or Rse receptor sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the Rse receptor or gas6 amino acid sequence is fused to (a) the hinge region and $C_H2$ and $C_H3$ or (b) the $C_H1$, hinge, $C_H2$ and $C_H3$ domains, of an $IgG_1$, $IgG_2$, or $IgG_3$ heavy chain. The precise site at which the fusion is made is not critical, and the optimal site can be determined by routine experimentation.

In some embodiments, the Rse- or gas6-immunoglobulin chimeras are assembled as multimers, and particularly as homo-dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Alternatively, the Rse or gas6 sequences can be inserted between immunoglobulin heavy chain and light chain sequences, such that an immunoglobulin comprising a chimeric heavy chain is obtained. In this embodiment, the Rse or gas6 sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom et al., *Mol. Immunol.* 28:1027–1037(1991).

Although the presence of an immunoglobulin light chain is not required in the immunoadhesins of the present invention, an immunoglobulin light chain might be present either covalently associated to a Rse or gas6-immunoglobulin heavy chain fusion polypeptide, or directly fused to the Rse receptor or gas6. In the former case, DNA encoding an immunoglobulin light chain is typically coexpressed with the DNA encoding the Rse- or gas6-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567.

In a preferred embodiment, the immunoglobulin sequences used in the construction of the immunoadhesins of the present invention are from an IgG immunoglobulin heavy chain constant domain. For human immunoadhesins, the use of human $IgG_1$ and $IgG_3$ immunoglobulin sequences is preferred. A major advantage of using $IgG_1$ is that $IgG_1$ immunoadhesins can be purified efficiently on immobilized protein A. In contrast, purification of $IgG_3$ requires protein G, a significantly less versatile medium. However, other structural and functional properties of immunoglobulins should be considered when choosing the Ig fusion partner for a particular immunoadhesin construction. For example, the $IgG_3$ hinge is longer and more flexible, so it can accommodate larger "adhesin" domains that may not fold or function properly when fused to $IgG_1$. Another consideration may be valency; IgG immunoadhesins are bivalent homodimers, whereas Ig subtypes like IgA and IgM may give rise to dimeric or pentameric structures, respectively, of the basic Ig homodimer unit. For Rse- or gas6-immunoadhesins designed for in vivo application, the pharmacokinetic properties and the effector functions specified by the Fc region are important as well. Although $IgG_1$, $IgG_2$ and $IgG_4$ all have in vivo half-lives of 21 days, their relative potencies at activating the complement system are different. $IgG_4$ does not activate complement, and $IgG_2$ is significantly weaker at complement activation than $IgG_1$. Moreover, unlike $IgG_1$, $IgG_2$ does not bind to Fc receptors on mononuclear cells or neutrophils. While $IgG_3$ is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, $IgG_1$ has only four serologically-defined allotypic sites, two of which (G1m and 2) are located in the Fc region; and one of these sites, G1m1, is non-immunogenic. In contrast, there are 12 serologically-defined allotypes in $IgG_3$, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

Gas6 and Rse immunoadhesins are most conveniently constructed by fusing the cDNA sequence encoding the gas6 or Rse portion in-frame to an Ig cDNA sequence. However, fusion to genomic Ig fragments can also be used (see, e.g. Gascoigne et al., supra; Aruffo et al., Cell 61:1303–1313 [1990]; and Stamenkovic et al., Cell 66:1133–1144[1991]). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the Ig parts of the immunoadhesin are inserted in tandem into a plasmid vector that directs efficient expression in the chosen host cells. For expression in mammalian cells, pRK5-based vectors (Schall et al., Cell 61:361–370 [1990]) and CDM8-based vectors (Seed, Nature 329:840 [1989]) are useful. The exact junction can be created by removing the extra sequences between the designed junction codons using oligonucleotide-directed deletional mutagenesis (Zoller and Smith, Nucleic Acids Res. 10:6487[1982]; and Capon et al., Nature 337:525–531 [1989]). Synthetic oligonucleotides can be used, in which each half is complementary to the sequence on either side of the desired junction; ideally, these are 36- to 48-mers. Alternatively, PCR techniques can be used to join the two parts of the molecule in-frame with an appropriate vector.

The choice of host cell line for the expression of the immunoadhesin depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., Cell 61:1303–1313[1990]; and Zettmeissl et al., DNA Cell Biol. (US) 9:347–353[1990]). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture. These clones are grown in the presence of increasing levels of DHFR inhibitor methotrexate and clones are selected in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells. For example, components such as light chain or J chain may be provided by certain myeloma or hybridoma host cells (Gascoigne et al., supra; and Martin et al., J. Virol. 67:3561–3568 [1993]).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., J. Immunol. Meth. 62:1–13 [1983]). Protein G is recommended for all mouse isotypes and for human γ3 (Guss et al., EMBO J. 5:15671575 [1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

The expression "Rse extracellular domain" or "Rse ECD" when used herein refers to a polypeptide sequence that shares a ligand- binding function of the extracellular domain of the Rse receptor. "Ligand-binding function" refers to the ability of the polypeptide to bind a Rse ligand, such as gas6. Accordingly, it is often not necessary to include the entire extracellular domain since smaller segments are commonly found to be adequate for ligand binding. The term ECD encompasses polypeptide sequences in which the cytoplasmic domain and hydrophobic transmembrane sequence (and, optionally, 1–20 amino acids amino-terminal to the transmembrane domain) of the Rse receptor have been deleted. Generally the ECD of the Rse receptor comprises amino acid residues from about 1–428 of the mature Rse receptor sequence disclosed in Mark et al., supra.

The term "epitope tagged" when used herein refers to a chimeric polypeptide comprising functionally active gas6 fused to a "tag polypeptide". The tag polypeptide has enough residues to provide an epitope against which an antibody thereagainst can be made, yet is short enough such that it does not interfere with functional activity of the gas6. The tag polypeptide preferably also is fairly unique so that the antibody thereagainst does not substantially cross-react with other epitopes. Suitable tag polypeptides generally have at least 6 amino acid residues and usually between about 8–50 amino acid residues (preferably between about 9–30 residues). The epitope tag is generally proved at the amino- or carboxyl-terminus of the gas6. Such epitope tagged forms of the gas6 are desirable, as the presence thereof can be detected using a labelled antibody against the tag polypeptide. Also, provision of the epitope tag enables the gas6 to be readily purified by affinity purification using the anti-tag antibody.

Tag polypeptides and their respective antibodies are well known in the art. Examples include the flu HA tag polypeptide and its antibody 12CA5, (Field et al., *Mol. Cell. Biol.* 8:2159–2165 [1988]); the c-myc tag and the 8F9, 3C7, 6E10, G4, B7 and 9E10 antibodies thereto (Evan et al., *Molecular and Cellular Biology* 5(12):3610–3616[1985]); and the Herpes Simplex virus glycoprotein D (gD) tag and its antibody (Paborsky et al., *Protein Engineering* 3(6):547–553 [1990]). Other tag polypeptides have been disclosed. Examples include the Flag-peptide (Hopp et al., *BioTechnology* 6:1204–1210 [1988]); the KT3 epitope peptide (Martin et al., *Science* 255:192–194[1992]); an α-tubulin epitope peptide (Skinner et al., *J. Biol. Chem* 266:15163–15166[1991]); and the T7 gene 10 protein peptide tag (Lutz-Freyermuth et al., *Proc. Natl. Acad. Sci. U.S.A.* 87:6393–6397 [1990]). Once the tag polypeptide has been selected, an antibody thereto can be generated using the techniques disclosed herein.

Gas6-tag polypeptide fusions are most conveniently constructed by fusing the cDNA sequence encoding the gas6 portion in-frame to the tag polypeptide DNA sequence and expressing the resultant DNA fusion construct in appropriate host cells. Ordinarily, when preparing the gas6-tag polypeptide chimeras of the present invention, nucleic acid encoding the gas6 (or a fragment thereof) will be fused at its 3' end to nucleic acid encoding the N-terminus of the tag polypeptide, however 5' fusions are also possible.

Epitope tagged gas6 can be conveniently purified by affinity chromatography using the anti-tag antibody. The matrix to which the affinity antibody is attached is most often agarose, but other matrices are available [e.g. controlled pore glass or poly(styrenedivinyl)benzene]. The epitope tagged gas6 can be eluted from the affinity column by varying the buffer pH or ionic strength or adding chaotropic agents, for example.

An "exogenous" compound is defined herein to mean a compound that is foreign to a cell and/or mammal to be treated with the compound, or homologous to a compound found in the cell or mammal but produced outside the cell or mammal.

"Isolated", when used to describe the various proteins disclosed herein, means protein that has been identified and separated and/or recovered from a component of its natural environment. Contaminant components of its natural environment are materials that would interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

Mammalian "Rse receptors" or "Rse receptor protein tyrosine kinases" (i.e. "rPTKs") have been described by Mark et al. in *J. Biol. Chem.* 269: 10720 (1994). When used throughout this application, the expression "Rse receptor" refers to endogenous Rse receptor present in a cell of interest as well as Rse receptor which is present in a cell by virtue of the cell having been transformed with nucleic acid encoding the Rse receptor, for example. Accordingly, the Rse receptor may be an amino acid or covalent variant of one of the native Rse receptors described by Mark et al., provided it is still "functionally active" (i.e. is able to be activated by a Rse ligand such as gas6). The preferred Rse receptor is endogenous human Rse receptor present in the cell membrane of a human cell.

The phrase "activating Rse receptor" refers to the step of causing the intracellular kinase domain of the Rse receptor to phosphorylate tyrosine residues in a substrate polypeptide. Often, the tyrosine residues are intrinsic to the Rse receptor (i.e. the "substrate" comprises the intracellular domain of the Rse receptor). Therefore , the degree of activation correlates with Rse receptor "autophosphorylation". Rse receptor autophosphorylation can be detected by Western blotting using an anti-phosphotyrosine antibody (see Example 3) or by KIRA ELISA (see Example 4). However, activation of the Rse receptor may correlate with phosphorylation of a substrate other than the Rse receptor (e.g. a tyrosine kinase existing adjacent the Rse receptor). This can be detected by measuring tyrosine phosphorylation of the substrate (e.g. by Western blotting).

The expression "enhancing survival of a cell" refers to the act of increasing the period of existence of a cell, relative to an untreated cell which has not been exposed to gas6, either in vitro or in vivo.

The phrase "enhancing proliferation of a cell" encompasses the step of increasing the extent of growth and/or reproduction of the cell, relative to an untreated cell, either in vitro or in vivo. An increase in cell proliferation in cell culture can be detected by counting the number of cells before and after exposure to gas6 (see Example 9 herein). The extent of proliferation can be quantified via microscopic examination of the degree of confluency. Cell proliferation can also be quantified by measuring $^3H$ uptake by the cells.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g. identifying morphological changes in the cell, see Example 9 below).

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The terms "treating", "treatment", and "therapy" refer to curative therapy, prophylactic therapy, and preventative therapy.

The term "mammal" refers to any mammal classified as a mammal, including humans, cows, horses, dogs and cats. In a preferred embodiment of the invention, the mammal is a human.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

2. Gas6 Production

Techniques suitable for the production of native gas6 or gas6 variants are well known in the art and include isolating gas6 from an endogenous source of this polypeptide (e.g. from serum), peptide synthesis (using a peptide synthesizer) and recombinant techniques (or any combination of these techniques). The preferred technique for production of native gas6 or a gas6 variant is a recombinant technique. The preferred gas6 variants are those which are essentially not γ carboxylated. This can be achieved in a number of ways but most conveniently involves creating a molecule which lacks one or more of the glutamic acid residues in the A domain of native gas6 which are normally γ carboxylated. Optionally, the entire A domain may be removed from the native molecule by enzymatic cleavage, but normally a nucleic acid molecule will be isolated which encodes the desired fragment (e.g. the D domain or a G domain therefrom). This nucleic acid molecule can be derived from the native gas6 nucleic acid.

Nucleic acid encoding native gas6 can be isolated from a cDNA library prepared from tissue believed to possess the polypeptide mRNA and to express it at a detectable level (e.g. brain tissue, see Example 6 below). Libraries are screened with probes (such as antibodies or oligonucleotides of about 20–80 bases) designed to identify the gas6 gene or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989).

Techniques for generating gas6 mutants via modification of the wildtype nucleic acid have been discussed above. The nucleic acid (e.g., cDNA or genomic DNA) encoding the native gas6 or gas6 variant is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The gas6 polypeptide may be produced as a fusion polypeptide with a signal sequence or other polypeptide having a specific cleavage site at the N-terminus of the mature protein or polypeptide. In general, the signal sequence may be a component of the vector, or it may be a part of the DNA that is inserted into the vector. The heterologous signal sequence selected preferably is one that is recognized and processed (i.e., cleaved by a signal peptidase) by the host cell. For prokaryotic host cells, the signal sequence may be substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, alpha factor leader (including Saccharomyces and Kluyveromyces α-factor leaders, the latter described in U.S. Pat. No. 5,010,182 issued Apr. 23, 1991), or acid phosphatase leader, the *C. albicans* glucoamylase leader (EP 362,179 published Apr. 4, 1990), or the signal described in WO 90/13646 published Nov. 15, 1990. In mammalian cell expression the native gas6 signal sequence is satisfactory, although other mammalian signal sequences may be suitable as well as viral secretory leaders, for example, the herpes simplex gD signal. The DNA for such precursor region is ligated in reading frame to DNA encoding the native gas6/gas6 variant.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors should contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.* 1:327 [1982]), mycophenolic acid (Mulligan et al., *Science* 209:1422[1980]) or hygromycin (Sugden et al., *Mol. Cell. Biol.* 5:410–413[1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the gas6 nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes gas6 variant. Increased quantities of gas6 are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. U.S.A.* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the gas6. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 11 7,060).

Alternatively, host cells (particularly wild-type hosts that contain endogenous DHFR) transformed or co-transformed with DNA sequences encoding gas6, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 [1979]; Kingsman et al., *Gene* 7:141 [1979]; or Tschemper et al., *Gene* 10:157 [1980]). The trp1 gene provides a selection marker for a mutant strain of yeast lacking the ability to grow in tryptophan, for example, ATCC No. 44076 or PEP4-1 (Jones, *Genetics* 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet.* 12:185 (1987). More recently, an expression system for large-scale production of recombinant calf chymosin was reported for *K. lactis*. Van den Berg, *Bio/Technology* 8:135 (1990). Stable multicopy expression vectors for secretion of mature recombinant human serum albumin by industrial strains of Kluyveromyces have also been disclosed. Fleer et al., *Bio/Technology* 9:968–975 (1991).

Expression and cloning vectors usually contain a promoter that is recognized by the host organism and is operably linked to the gas6 nucleic acid. A large number of promoters recognized by a variety of potential host cells are well known. These promoters are operably linked to gas6-encoding DNA by removing the promoter from the source DNA by restriction enzyme digestion and inserting the isolated promoter sequence into the vector.

Promoters suitable for use with prokaryotic hosts include the β-lactamase and lactose promoter systems (Chang et al., *Nature* 275:615 [1978]; and Goeddel et al., *Nature* 281:544 [1979]), alkaline phosphatase, a tryptophan (trp) promoter system (Goeddel, *Nucleic Acids Res.,* 8:4057 [1980] and EP 36,776) and hybrid promoters such as the tac promoter (deBoer et al., *Proc. Natl. Acad. Sci. U.S.A.* 80:21–25 [1983]). However, other known bacterial promoters are suitable. Their nucleotide sequences have been published, thereby enabling a skilled worker operably to ligate them to DNA encoding the gas6 (Siebenlist et al., *Cell* 20:269 [1980]) using linkers or adaptors to supply any required restriction sites. Promoters for use in bacterial systems also will contain a Shine-Dalgarno (S.D.) sequence operably linked to the DNA encoding the gas6.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073[1980]) or other glycolytic enzymes (Hess et al., *J. Adv. Enzyme Reg.* 7:149 [1968]; and Holland, *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Gas6 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter or from heat-shock promoters.

The early and late promoters of the SV40 virus are conveniently obtained as an SV40 restriction fragment that also contains the SV40 viral origin of replication. Fiers et al., *Nature* 273:113 (1978); Mulligan and Berg, *Science* 209:1422–1427 (1980); Paviakis et al., *Proc. Natl. Acad. Sci. U.S.A.* 78:7398–7402(1981). The immediate early promoter of the human cytomegalovirus is conveniently obtained as a HindIII E restriction fragment. Greenaway et al., *Gene* 18:355–360(1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human β-interferon cDNA in mouse cells under the control of a thymidine kinase promoter from herpes simplex virus; Canaani and Berg, *Proc. Natl. Acad. Sci. U.S.A.* 79:5166–5170(1982) on expression of the human interferon β1 gene in cultured mouse and rabbit cells; and Gorman et al., *Proc. Natl. Acad. Sci. U.S.A.* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the gas6 by higher eukaryotes is often increased by inserting an enhancer sequence into the vector. Enhancers are relatively orientation and position independent, having been found 5' (Laimins et al., *Proc. Natl. Acad. Sci. U.S.A.* 78:993 [1981]) and 3' (Lusky et al., *Mol. Cell Bio.* 3:1108 [1983]) to the transcription unit, within an intron (Banerji et al., *Cell* 33:729 [1983]), as well as within the coding sequence itself (Osborne et al., *Mol. Cell Bio.* 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the gas6-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the gas6.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499 (1980).

Particularly useful in the practice of this invention are expression vectors that provide for the transient expression in mammalian cells of DNA encoding gas6. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of gas6 variants having desired binding specificities/affinities.

Other methods, vectors, and host cells suitable for adaptation to the synthesis of the gas6 in recombinant vertebrate cell culture are described in Gething et al., *Nature* 293:620–625 (1981); Mantei et al., *Nature* 281:40–46 (1979); Levinson et al.; EP 117,060; and EP 117,058. A particularly useful plasmid for mammalian cell culture expression of gas6 is pRK5 (EP 307,247) or pSVI6B (PCT pub. no. WO 91/08291 published Jun. 13, 1991).

The choice of host cell line for the expression of gas6 depends mainly on the expression vector. Where it is desired to make a gas6 variant which is essentially not γ carboxylated, it may be desirable to select a host cell which does not have γ carboxylase enzyme, especially where the nucleic acid encoding gas6 also encodes the A domain thereof. Often, a useful host for this purpose is a non-mammalian cell (e.g. a prokaryotic cell known to be deficient in this enzyme). Alternatively a mammalian cell line can be utilized which has been made deficient in this enzyme.

Suitable host cells for cloning or expressing the vectors herein are prokaryote, yeast, or other higher eukaryote cells described above. Suitable prokaryotes for this purpose include eubacteria, such as Gram-negative or Gram-positive organisms, for example, Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa,* and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompTΔdegP41kan. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively, methods of cloning, e.g., PCR or other nucleic acid polymerase reactions, are suitable.

In addition to prokaryotes, eukaryotic microbes such as filamentous fungi or yeast are suitable cloning or expression hosts for gas6-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature* 290:140 [1981]; EP 139,383 published May 2, 1985); Kluyveromyces hosts (U.S. Pat. No. 4,943,529; Fleer et al., supra) such as, e.g., *K. lactis* (MW98-8C, CBS683, CBS4574; Louvencourt et al., *J. Bacteriol.*, 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia (EP 402,226); *Pichia pastoris* (EP 183,070; Sreekrishna et al., *J. Basic Microbiol.* 28:265–278 [1988]); Candida; *Trichoderma reesia* (EP 244,234); *Neurospora crassa* (Case et al., *Proc. Natl. Acad. Sci. U.S.A.* 76:5259–5263 [1979]); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.* 112:284–289 [1983]; Tilburn et al., *Gene* 26:205–221[1983]; Yelton et al., *Proc. Natl. Acad. Sci. U.S.A.* 81:1470–1474 [1984]) and *A. niger* (Kelly and Hynes, *EMBO J.* 4:475–479 [1985]).

Suitable host cells for the expression of glycosylated gas6 are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology* 6:47–55 (1988); Miller et al., in *Genetic Engineering*, Setlow et al., eds., Vol. 8 (Plenum Publishing, 1986), pp. 277–279; and Maeda et al., *Nature* 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the gas6 DNA. During incubation of the plant cell culture with *A. tumefaciens*, the DNA encoding the gas6 is transferred to the plant cell host such that it is transfected, and will, under appropriate conditions, express the gas6 DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 [1977]); baby hamster kidney cells (BHK, ATCC CCL 10); Chinese hamster ovary cells/-DHFR (CHO, Urlaub and Chasin, *Proc. Natl. Acad. Sci. U.S.A.* 77:4216 [1980]); mouse sertoli cells (TM4, Mather, *Biol. ReDrod.* 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68[1982]); MRC 5 cells; FS4 cells; and a human hepatoma line (Hep G2).

Host cells are transfected with the above-described expression or cloning vectors of this invention and cultured in conventional nutrient media modified as appropriate for inducing promoters, selecting transformants, or amplifying the genes encoding the desired sequences. Depending on the host cell used, transfection is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham and van der Eb, *Virology* 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.* 130:946 (1977) and Hsiao et al., *Proc. Natl. Acad. Sci. (U.S.A.)* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* 185:527–537 (1990), and Mansour et al., *Nature* 336:348–352(1988).

Prokaryotic cells used to produce the gas6 polypeptide of this invention are cultured in suitable media as described generally in Sambrook et al., supra.

The mammalian host cells used to produce the gas6 of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* 58:44 (1979), Barnes and Sato, *Anal. Biochem.* 102:255 (1980), U.S. Pat. Nos. 4,767,704; 4,657,866; 4,927,762; or 4,560,655; WO 90/03430; WO 87/00195; U.S. Pat. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art.

In certain embodiments, it is desirable to culture the transformed host cells in the absence of Vitamin K as this can reduce γ carboxylation of the A domain of the gas6 polypeptide. Alternatively, the transformed host cells can be cultured in the presence of a carboxylase inhibitor, such as warfarin The culture conditions, such as temperature, pH, and the like, are those previously used with the host cell selected for expression, and will be apparent to the ordinarily skilled artisan. In general, principles, protocols, and practical techniques for maximizing the productivity of mammalian cell cultures can be found in *Mammalian Cell Biotechnology: a Practical Approach,* M. Butler, ed., IL Press, 1991. The host cells referred to in this disclosure encompass cells in culture as well as cells that are within a host animal.

Gas6 preferably is recovered from the culture medium as a secreted polypeptide, although it also may be recovered from host cell lysates.

When gas6 is produced in a recombinant cell other than one of human origin, it is completely free of proteins or polypeptides of human origin. However, it is necessary to purify gas6 from cell proteins or polypeptides to obtain preparations that are substantially homogeneous as to gas6. As a first step, the particulate debris, either host cells or lysed fragments, is removed, for example, by centrifugation or ultrafiltration; optionally, the protein may be concentrated with a commercially available protein concentration filter, followed by separating the gas6 from other impurities by one or more steps selected from heparin Sepharose chromatography, immunoaffinity chromatography, ion-exchange column fractionation (e.g., on DEAE or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the gas6, and ethanol or ammonium sulfate precipitation. A protease inhibitor may be included in any of the foregoing steps to inhibit proteolysis and antibiotics may be included to prevent the growth of adventitious contaminants. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin, and benzamidine.

Gas6 variants in which residues have been deleted, inserted, or substituted are recovered in the same fashion as native gas6, taking account of any substantial changes in properties occasioned by the variation. For example, preparation of "epitope tagged" gas6 facilitates purification using an immunoaffinity column containing antibody to the antigen to adsorb the fusion polypeptide. Immunoaffinity columns such as a rabbit polyclonal anti-gas6 column can be employed to absorb the gas6 variant by binding it to at least one remaining immune epitope. One skilled in the art will appreciate that purification methods suitable for native gas6 may require modification to account for changes in the character of gas6 or its variants upon production in recombinant cell culture.

3. In Vitro and In Vivo Uses for Gas6

The present invention provides methods for activating Rse receptor and/or enhancing survival, proliferation or differentiation of cells comprising the Rse receptor using gas6. The gas6 useful in the practice of the present invention can be prepared in a number of ways which have been described in the previous section (see also Example 6 below).

The gas6 may be from a human or any non-human species. For instance, a mammal may be treated with gas6 from a different mammalian species (e.g., mice can be treated with human gas6). There is substantial homology (about 81% amino acid identity) between murine gas6 and human gas6, and thus, it is expected that gas6 from different mammalian species can be employed. Preferably, however, the mammal is treated with homologous gas6 (e.g., humans are treated with human gas6) to avoid potential immunogenicity of the gas6 in the mammal.

The present invention includes methods of activating Rse receptor and/or enhancing survival, proliferation or differentiation of cells comprising the Rse receptor in vivo and in vitro.

Normally, the cells will be treated with the gas6 polypeptide. However, gene therapy approaches have been described in the art and are encompassed by the present invention. These techniques include gene delivery to a cell using adenovirus, herpes simplex I virus or adeno-associated virus as well as lipid-based delivery systems (e.g. liposomes). Retroviruses are useful for ex vivo gene therapy approaches. Accordingly, it is possible to administer the nucleic acid encoding gas6, resulting in expression of the gas6 polypeptide in the patient or in tissue culture. For exemplary gene therapy techniques see WO 93/25673 and the references cited therein.

In accordance with the in vitro methods of the invention, cells comprising the Rse receptor are provided and placed in a cell culture medium. Examples of such Rse-receptor-containing cells include neural cells, e.g., brain cells (such as neurons of the neocortex, cerebellum and hippocampus); glial cells (e.g. Schwann cells or astrocytes); kidney or breast-derived cells; cells derived from the ovary or testes; fibroblast cells such as mouse 3T3 cells; cells from the hematopoietic system such as CMK11-5. The preferred cell to be cultured is a Schwann cell. See Example 9 herein.

Suitable tissue culture media are well known to persons skilled in the art and include, but are not limited to, Minimal Essential Medium (MEM), RPMI-1 640, and Dulbecco's Modified Eagle's Medium (DMEM). These tissue culture medias are commercially available from Sigma Chemical Company (St. Louis, Mo.) and GIBCO (Grand Island, N.Y.).

The cells are then cultured in the cell culture medium under conditions sufficient for the cells to remain viable and grow in the presence of an effective amount of gas6. The cells can be cultured in a variety of ways, including culturing in a clot, agar, or liquid culture.

The cells are cultured at a physiologically acceptable temperature such as 37° C., for example, in the presence of an effective amount of gas6. The amount of gas6 may vary, but preferably is in the range of about 10 ng/ml to about 1mg/ml. The gas6 can of course be added to the culture at a dose determined empirically by those in the art without undue experimentation. The concentration of gas6 in the culture will depend on various factors, such as the conditions under which the cells and gas6 are cultured. The specific temperature and duration of incubation, as well as other culture conditions, can be varied depending on such factors as, e.g., the concentration of the gas6, and the type of cells and medium. Those skilled in the art will be able to determine operative and optimal culture conditions without undue experimentation. Proliferation, differentiation and/or survival of the cells (e.g. neurons) in the cultures can be determined by various assays known in the art such as those described above.

It is contemplated that using gas6 to enhance cell survival, growth and/or differentiation in vitro will be useful in a variety of ways. For instance, neural cells cultured in vitro in the presence of gas6 can be infused into a mammal suffering from reduced levels of the cells. Stable in vitro cultures can be used for isolating cell-specific factors and for expression of endogenous or recombinantly introduced proteins in the cell. Gas6 may also be used to enhance cell survival, proliferation and/or differentiation of cells which support the growth and/or differentiation of other cells in cell culture (e.g. stromal cells supporting bone marrow nonadherent cells). In this manner, Schwann cells may promote neuronal survival in cell culture.

Gas6 is considered to be particularly useful for growing Schwann cells ex vivo. It is desirable to have such populations of cells in cell culture for isolation of cell-specific factors e.g. $P75^{NGFR}$ which is a Schwann cell specific marker. Such factors are useful as diagnostic tools or, in the case of $P75^{NGFR}$, can be used an antigens to generate antibodies for diagnostic use. It is also desirable to have stable populations of Schwann cells in cell culture to facilitate characterization of other mitogens and growth inhibitory agents for these cells.

The invention also provides in vivo uses for gas6. Based on the ability of gas6 to promote proliferation of glial cells (see Example 9), it is believed that this molecule will be particularly useful for treating diseases which involve demyelination, damage or loss of glial cells (e.g. multiple sclerosis).

Gas6 is also believed to be useful in promoting the development, maintenance, and/or regeneration of neurons in vivo, including central (brain and spinal chord), peripheral (sympathetic, parasympathetic, sensory, and enteric neurons), and motorneurons. Accordingly, gas6 may be utilized in methods for the diagnosis and/or treatment of a variety of "neurologic diseases or disorders" which effect the nervous system of a mammal, such as a human.

Such diseases or disorders may arise in a patient in whom the nervous system has been damaged by, e.g., trauma, surgery, stroke, ischemia, infection, metabolic disease, nutritional deficiency, malignancy, or toxic agents. The agent is designed to promote the survival or growth of neurons. For example, gas6 can be used to promote the survival or growth of motorneurons that are damaged by trauma or surgery.

Also, gas6 can be used to treat motoneuron disorders, such as amyotrophic lateral sclerosis (Lou Gehrig's disease), Bell's palsy, and various conditions involving spinal muscular atrophy, or paralysis. Gas6 can be used to treat human "neurodegenerative disorders", such as Alzheimer's disease, Parkinson's disease, epilepsy, multiple sclerosis, Huntington's chorea, Down's Syndrome, nerve deafness, and Meniere's disease.

Further, gas6 can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

In still further embodiments of the invention, gas6 antagonists, and especially anti-gas6 antibodies, can be administered to patients suffering from neurologic diseases and disorders characterized by excessive production of gas6. Gas6 antagonists can be used in the prevention of aberrant regeneration of sensory neurons such as may occur postoperatively, or in the selective ablation of sensory neurons, for example, in the treatment of chronic pain syndromes.

Therapeutic formulations of gas6 and gas6 antagonists for treating neurologic diseases and disorders are prepared by mixing gas6 or anti-gas6 antibody, having the desired degree of purity, with optional pharmaceutically acceptable carriers, excipients, or stabilizers which are well known. Acceptable carriers, excipients or stabilizers are nontoxic to the patient at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

It may be desirable to adsorb gas6 onto a membrane, such as a silastic membrane, which can be implanted in proximity to damaged neural tissue, or to incorporate gas6 into liposomes. PCT Pub. No. WO 91/04014(published Apr. 4, 1991). In another embodiment, the gas6 used for therapeutic effect is gas6 covalently joined to another protein, such as an immunoglobulin domain (for example, to produce gas6-IgG).

Gas6 optionally is combined with or administered in concert with other neurotrophic factors to achieve a desired therapeutic effect. For example, gas6 may be used together with nerve growth factor (NGF), neurotrophins (NT-3), bone derived nerve factor (BDNF), neurotrophins-4 and -5 (NT4/5), an insulin-like growth factor (e.g., IGF-1 or IGF-2) or another neurotrophic factor to achieve a synergistic stimulatory effect on the growth of sensory neurons, wherein the term "synergistic" means that the effect of the combination of gas6 with a second substance is greater than that achieved with either substance used individually.

Gas6 and gas6 antagonists to be used for in vivo administration must be sterile. This is readily accomplished by filtration of a solution of gas6 or anti-gas6 antibody through sterile filtration membranes. Thereafter, the filtered solution may be placed into a container having a sterile access port, for example, an intravenous solution bag or vial having a stopper pierceable by a hypodermic injection needle. The filtered solution also may be lyophilized to produce sterile gas6 or anti-gas6 antibody in a powder form.

Methods for administering gas6 and gas6 antagonists in vivo include injection or infusion by intravenous, intraperitoneal, intracerebral, intrathecal, intramuscular, intraocular, intraarterial, or intralesional routes, and by means of sustained-release formulations.

Sustained-release formulations generally consist of gas6 or gas6 antagonists and a matrix from which the gas6 or gas6 antagonists are released over some period of time. Suitable matrices include semipermeable polymer matrices in the form of shaped articles, for example, membranes, fibers, or microcapsules. Sustained release matrices may comprise polyesters, hydrogels, polylactides, U.S. Pat. No. 3,773,919, copolymers of L-glutamic acid and γethyl-L-glutamate, Sidman et al., *Biopolymers* 22:547–556(1983), poly (2-hydroxyethyl-methacrylate), or ethylene vinyl acetate, Langer et al., *J. Biomed. Mater. Res.* 15:167–277 (1981); and Langer, *Chem. Tech.* 12:98–105 (1982).

In one embodiment of the invention, the therapeutic formulation comprises gas6 or gas6 antagonist entrapped within or complexed with liposomes. For example, gas6 covalently joined to a glycophosphatidyl-inositol moiety may be used to form a liposome comprising gas6. In a further embodiment, the therapeutic formulation comprises cells actively producing gas6 or gas6 antagonist. Such cells may be directly introduced into the tissue of a patient, or may be encapsulated within porous membranes which are then implanted in a patient, in either case providing for the delivery of gas6 or anti-gas6 antagonist into areas within the body of the patient in need of increased or decreased concentrations of gas6. Alternatively, an expression vector comprising gas6 DNA may be used for in vivo transformation of a patient's cells to accomplish the same result.

An effective amount of gas6 or anti-gas6 antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Where possible, it is desirable to determine appropriate dosage ranges first in vitro, for example, using assays for cell survival or growth which are known in the art, and then in suitable animal models, from which dosage ranges for human patients may be extrapolated. In a specific embodiment of the invention, a pharmaceutical composition effective in promoting the survival or growth of neurons will provide a local gas6 concentration in vivo of between about 0.1 and 10 ng/ml.

The invention further provides an article of manufacture and kit containing materials useful for activating the Rse receptor or enhancing survival, proliferation or differentiation of cells comprising the Rse receptor. The article of manufacture comprises a container with a label. Suitable containers include, for example, bottles, vials, and test tubes. The containers may be formed from a variety of materials such as glass or plastic. The container holds a composition which is effective for activating the Rse receptor and/or enhancing survival, proliferation and/or differentiation of cells having this receptor. The active agent in the composition is gas6. The label on the container indicates that the composition is used for activating the Rse receptor and/or enhancing survival, proliferation and/or differentiation of cells having this receptor, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All literature citations herein are incorporated by reference.

EXAMPLE 1

Production of Rse-IpG Fusion Protein

To identify a source of a Rse ligand (Rse-L), a fusion protein containing the extracellular domain of human Rse followed by the Fc portion of human IgG (Rse-IgG) was used as a probe to screen cells for surface bound Rse-L using flow cytometry (see Example 2 below). Rse-IgG was constructed by fusing the sequence encoding the extracellular domain (amino acids 1–428) of human Rse (Mark et al., *Journal of Biological Chemistry* 269(14):10720–10728 [1994]) to amino acids 216–443 of human IgGγ$_1$ through a BstEII linker (adding amino acids Val and Thr). The linker was added to Rse sequences by PCR using the primers (5'-TCAAGACAATGGAACCCAGG [SEQ ID NO: 4] and 5'-CATGGAATTCGGTGACCGATGTGCGGCTGTGA-GGAG [SEQ ID NO: 5]). The cDNA encoding Rse-IgG was transferred into an SV40 based expression vector and introduced into DHFR CHO cells by electroporation (250 volts, 960 μF). DHFR$^+$ cells were selected and Rse-IgG expression in individual clones was determined using a human Fc-specific ELISA. Rse-IgG was purified on a protein A-Sepharose column (Pharmacia).

EXAMPLE 2

Binding Analysis

Fluorescence activated cell sorting (FACS) analysis using Rse-IgG was performed as described in Goodwin et al., *Cell* 73:447 (1993). The megakaryocytic leukemia line CMK11-5 cells (Adachi et al., *Exp Hematol.* 19:923 [1991]) specifically bound Rse-IgG but not control fusion proteins containing the identical Fc domain such as HGFr-IgG (Mark et al., *J. Biol. Chem.* 267:26166 [1992]) or CD4-IgG (Capon et al., *Nature* 337:525 [1989]). Binding of Rse-IgG was increased by the addition of Ca$^{2+}$ and abolished by treatment with 2 mM EDTA.

Subsequently, an in vitro binding assay was established to characterize the interaction of $^{125}$I-Rse-IgG with the putative cell surface bound Rse-L. CMK11-5 cells were suspended in 10 mM TrisCl, pH 7.5 for 10 min on ice, lysed by a combination of sonication and shearing, and whole membranes collected by centrifugation and stored in 50 mM TrisCl, pH 7.5, 20% glycerol at −80° C. Membranes equivalent to 200,000 cells were combined with fetal bovine serum (FBS) or column fractions, competitors, and $^{125}$I-Rse-IgG in a total volume of 0.1–0.12 ml. After a 30 min incubation at room temperature, 1 ml of ice cold assay buffer was added to each tube. Then, the membrane associated radioactivity was collected by centrifugation for 4 min at 15000 g, separated from unbound radioactivity by aspiration of the supernatant fluid and counted in a γ counter. The assay buffer was 50 mM Tris-HCl, 0.05% Tween-20, 0.1% BSA, 5 mM CaCl$_2$.

Because flow cytometric analyses were performed in the presence of serum, the effect of FBS in the membrane binding assay was determined. Binding was found to be absolutely dependent on FBS concentration; no displaceable binding was seen in the absence of FBS and half maximum binding was observed with 0.58% FBS (FIG. 3A).

Binding was also Ca$^{2+}$-dependent; half maximum binding was obtained with 0.18 mM Ca$^{2+}$ (FIG. 3B). Although the apparent number of binding sites for Rse-IgG was dependent on the concentration of FBS, the affinity was not greatly changed [K$_d$ of 0.82 nM in 1% FBS vs. 2.2 nM in 10% FBS] (FIG. 3C). Binding was specific; other recombinant IgG fusion proteins, such as CD4-IgG, did not compete for binding with $^{125}$I-Rse-IgG.

EXAMPLE 3

Epitope-Tagged Rse Receptor and Activation Thereof

Chinese Hamster Ovary (CHO) cells expressing a version of Rse receptor having a Herpes simplex virus type I (HSV-1) C-terminal glycoprotein D (gD) flag (Paborsky et al., *Protein Engineering* 3(6):547–553 [1990]) were generated in order to further characterize a Rse-L.

Synthetic double stranded oligonucleotides were used to reconstitute the coding sequence for the C-terminal 10 amino acids (880–890) of human Rse and add an additional 21 amino acids containing the gD epitope for the antibody 5B6 (Paborksy et al., supra) and a stop codon. The final sequence of the synthetic portion of the fusion gene was: coding strand:
5'-GCAAGGGCTACTGCCACACTCGAGCTGCGCAG-ATGCTAGCCTCAAGATGGCTGATCCAAATCGATT-CCGCGGCAAAGATCTTCCGGTCCTGTAGA-3'[SEQ ID NO: 6] noncoding strand:
5'-AGCTTCTACAGGACCGGAAGATCTTTGCCGCG-GAATCGATTTGGATCAGCCATCTTGAGGCTAGC-ATCTGCGCAGCTCGAGTGTGGCAGTAGCCCTTG-CTGCA-3'[SEQ ID NO: 7].

The synthetic DNA was ligated with the cDNA encoding amino acids 1–880 of human Rse at the PstI site beginning at nucleotide 2644 of the published human Rse cDNA sequence (Mark et al., *Journal of Biological Chemistry* 269(14):10720–10728[1994]) and HindIII sites in the polylinker of the expression vector pSV17.ID.LL (see PCT/US94/13329) derived from the vector pRK (Suva et al., *Science*, 237:893–896 [1987]) to create the expression plasmid pSV.ID.Rse.gD. Briefly, the expression plasmid comprises a dicistronic primary transcript which contains sequence encoding DHFR bounded by 5' splice donor and 3' splice acceptor intron splice sites, followed by sequence that encodes the Rse.gD. The full length (non-spliced) message contains DHFR as the first open reading frame and therefore generates DHFR protein to allow selection of stable transformants.

dp12.CHO cells (EP 307,247 published Mar. 15, 1989) were electroporated with pSV.ID.Rse.gD which had been linearized at a unique NotI site in the plasmid backbone. The DNA was ethanol precipitated after phenol/chloroform extraction and was resuspended in 10 μl 10/1 Tris/EDTA. Then, 20 μg of DNA was incubated with 10$^7$ CHO.dp 12 cells in 1 ml of PBS on ice for 10 min. before electroporation at 350 volts and 330 μf. Cells were returned to ice for 10 min. before being plated into non-selective medium. After 24 hours cells were fed nucleoside-free medium to select for stable DHFR+ clones.

To identify a cell line that expresses Rse.gD nucleic acid, candidate clones were screened by FACS analysis using the polyclonal antiserum 19B which recognizes epitopes in the extracellular domain of Rse. To confirm that clones that scored positive in the FACS assay express full-length Rse.gD nucleic acid, cell lysates were prepared (Lokker et al., *EMBO J*, 11:2503–2510 [1992]) and solubilized Rse.gD was immunoprecipitated with the 19B antisera. The immunoprecipitated proteins were fractionated under reducing conditions using 7% PAGE, blotted onto nitrocellulose and then probed with the anti-gD 5B6 antibody (Paborsky et al., supra) which was detected with a horseradish peroxidase conjugated anti-mouse IgG antibody.

The ability of Rse.gD in cell clones to undergo autophosphorylation in response to 20% FBS, partially purified fractions of FBS containing the Rse receptor binding activity (i.e. 1:10 dilution of the QSE fraction obtained in Example 5 below) or control (i.e. no additions) was determined by Western blotting. Briefly, 5×10$^5$ dp12.CHO cells transformed with Rse.gD nucleic acid as described above were seeded on a 60 mm dish in the presence of serum for 6h. The cells were then washed in phosphate buffered saline (PBS) and serum-starved for 16h. The serum starved cells were then exposed to the sample for 10 min. The Rse.gD protein was immunoprecipitated from CHO cell lysates using the anti-gD 5B6 monoclonal antibody. Proteins were fractionated on 7% SDS-PAGE under reducing conditions and transferred to nitrocellulose. Phosphorylation of Rse was detected with labelled anti-phosphotyrosine antibody 4G10 (obtained commercially from UBI, New York).

Addition of either 20% FBS or partially purified fractions of FBS containing the Rse-IgG binding activity to serum-starved cells expressing Rse-gD resulted in phosphorylation of the 140 kDa Rse receptor on tyrosine residues. The Rse receptor was not activated by the control.

EXAMPLE 4

KIRA ELISA

Figure 4:
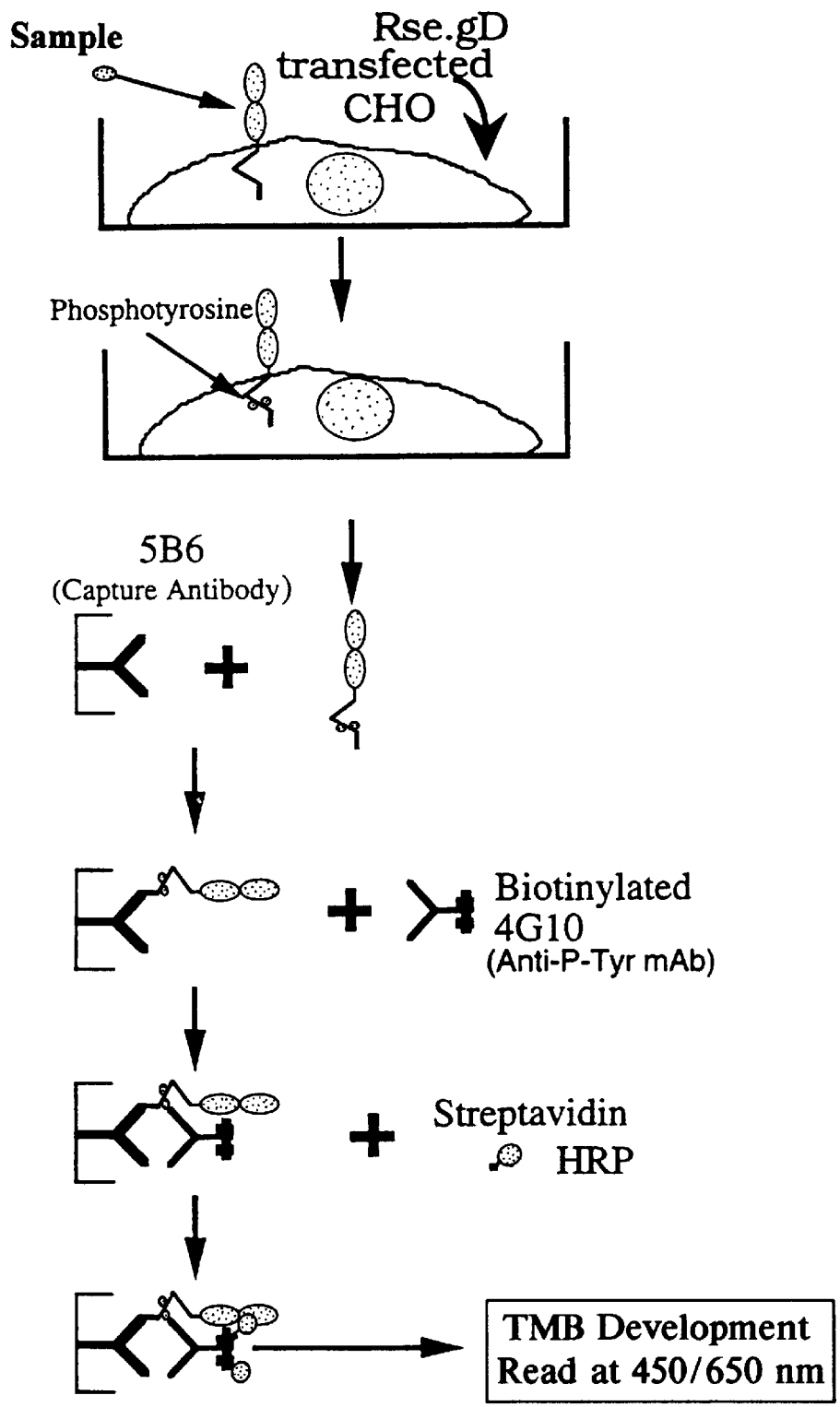
FIG. 4 is a flow chart/cartoon illustrating the KIRA ELISA for the Rse receptor described in Example 4.

The activity in FBS that activated Rse.gD was further characterized using an ELISA-based "KIRA" (for Kinase Receptor Activation) assay that allows high-throughput analysis of potential Rse-L sources. See FIG. 4 for a schematic representation of this assay.

Rse.gD transformed dp12.CHO cells produced as described in Example 3 were seeded (5×10$^4$ per well) in the wells of a flat-bottom-96 well culture plate in 100 μl media and cultured overnight at 37° C. in 5% CO$_2$. The following morning the well supernatants were decanted, and the plates were lightly tamped on a paper towel. 50 μl of media containing QSE fraction obtained as described in Example 5 below or control (i.e. media alone) was then added to each well. For neutralization experiments, potential ligand sources were treated at room temperature for 30 min with Rse-IgG or CD4-IgG (100 μg/ml) prior to addition to the cells. The cells were stimulated at 37° C. for 30 min., the well supernatants were decanted, and the plates were once again lightly tamped on a paper towel. To lyse the cells and solubilize the receptors, 100 µl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 µM leupeptin (ICN Biochemicals), and 2 mM sodium orthovanadate (Na$_3$VO$_4$; Sigma Chemical Co, St. Louis, Mo.), pH 7.5. The plate was then agitated gently on a plate shaker (Belico Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 µg/ml in 50 mM carbonate buffer, pH 9.6, 100 µl/well) was decanted, tamped on a paper towel and blocked with 150 µl/well of Block Buffer (PBS containing 0.5% BSA [Intergen Company, Purchase, N.Y.] and 0.01% thimerosal) for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized Rse.gD from the cell-culture microtiter well was transferred (85 µl/well) to anti-gD 5B6 coated and blocked ELISA well and was incubated for 2 h at room temperature with gentle agitation. The unbound Rse.gD was removed by washing with wash buffer and 100 µl of biotinylated 4G10 (anti-phosphotyrosine) at 0.15 µg/ml in buffer (PBS containing 0.5% BSA, 0.05% Tween-20, 5 mM EDTA, and 0.01% thimerosal), was added to each well. After incubation for 2 h at room temperature the plate was washed and 100 µl of HRPO-conjugated streptavidin (Zymed Laboratories, S. San Francisco, Calif.) diluted 1:6×10$^4$ in dilution buffer was added to each well. The plate was incubated for 30 minutes at room temperature with gentle agitation. The free avidin-conjugate was washed away and 100 µl freshly prepared substrate solution (tetramethyl benzidine [TMB]; 2-component substrate kit; Kirkegard and Perry, Gaithersburg, Md.) was added to each well. The reaction was allowed to proceed for 10 minutes, after which the color development was stopped by the addition of 100 µl/well 1.0M H$_3$PO$_4$. The absorbance at 450 nm was read with a reference wavelength of 650 nm (ABS$_{450/650}$) using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

Figure 3D:
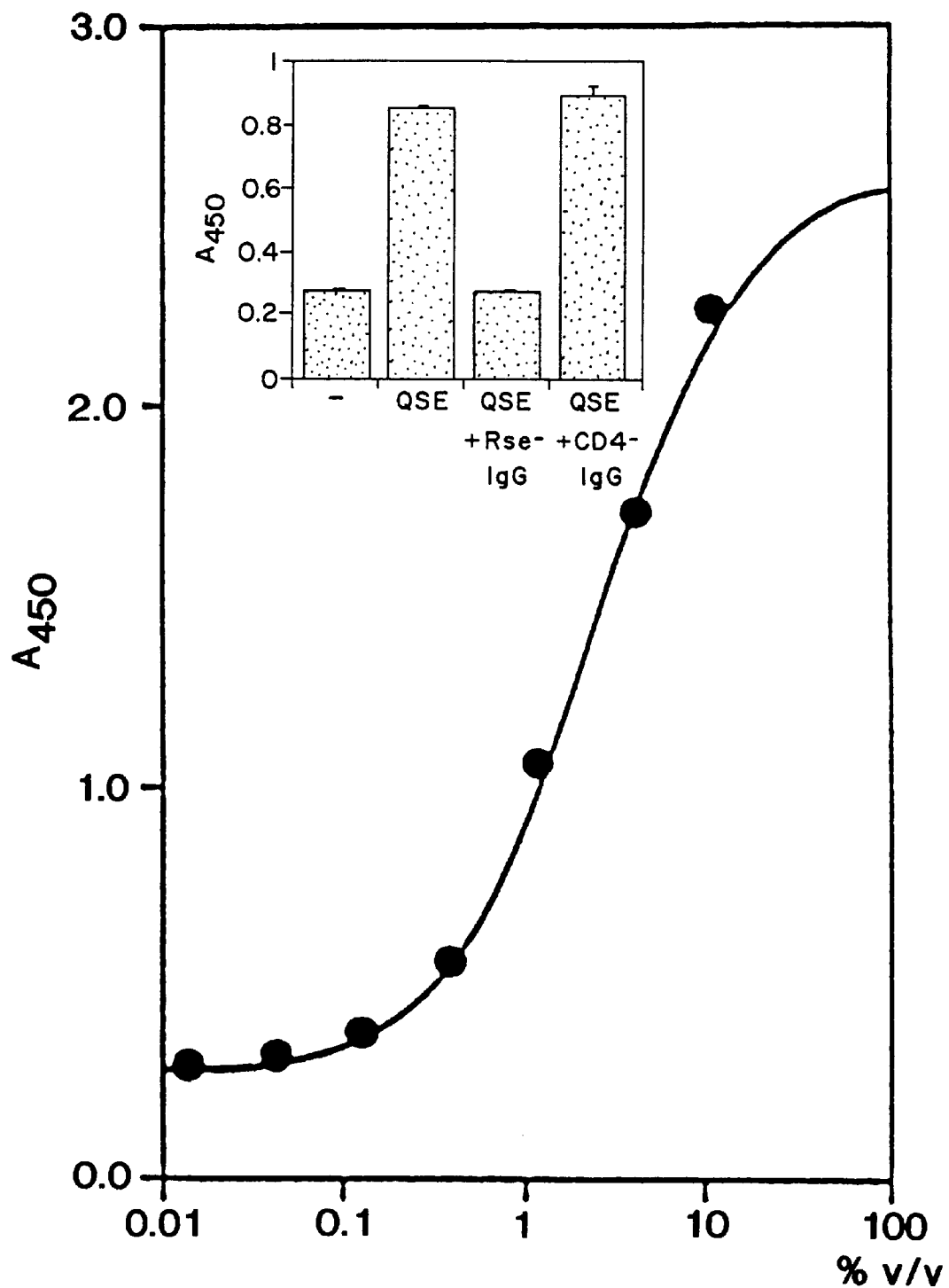

Phosphorylation of Rse.gD was stimulated in a dose dependent fashion and this activity was neutralized by Rse-IgG but not by the control CD4-IgG (FIG. 3D). These data show that a ligand capable of activating Rse is present in FBS.

EXAMPLE 5

Rse Ligand Characterization

The Rse-L was purified from FBS by ion exchange and Rse affinity chromatography (see Table 2 below).

TABLE 2

Purification of a Rse Ligand from FBS

| | Protein (mg) | Units | Yield (%) | Specific Activity (SA) (Units/mg) | Fold Purification |
|---|---|---|---|---|---|
| FBS | 2800 | 196 | 100 | 0.07 | 1 |
| QSE | 12.8 | 94 | 48 | 7.4 | 105 |
| Rse-IgG Affinity | 0.183 | 22 | 11 | 119 | 1701 |

Fetal bovine serum (FBS) was dialyzed (molecular weight cut off 6000 Da) against 50 mM Tris HCl pH 7.5 and sterile filtered (0.22 µ cellulose nitrate, Corning) before loading onto a Q-Sepharose column equilibrated in buffer A, 10 mM Tris HCl, pH 7.5. Buffer B was buffer A with 1M NaCl. The column was eluted with a 1 column volume gradient from 0 to 18% B, then a 10 column volume gradient of 18 to 60% B. Active fractions, eluting near 0.4M NaCl, were pooled and dialyzed against 50 mM Tris HCl pH 7.5, 5 mM benzamidine. This Q-Sepharose enriched fraction (QSE) was applied to a Rse-IgG affinity column. The column was washed with 50 mM Tris HCl, pH 7.5, 5 mM benzamidine and eluted with 4M Urea, 0.1M Tris HCl, pH 7.5, 5 mM benzamidine. The eluate was concentrated and dialyzed by centrifugal ultrafiltration (Centricon 10). Rse-IgG columns were prepared using 2 mg of Rse-IgG per ml Emphase resin according to the supplier's instructions (Pierce). The quantities tabulated are relative to 100 ml of FBS starting material. One unit of binding activity is defined as the amount present in 1 ml of a sample having an EC$_{50}$ of 1% v/v in the in vitro binding activation assay described in Example 2 above.

Sodium dodecyl sulfate polyacrylamide gel electrophoresis (SDS-PAGE) of the affinity-purified Rse-L preparation showed a broad band centered at 60 kDa with unreduced samples which resolved into several closely spaced bands from 65 to 68 kDa upon reduction. Fractions were heated for 10 min at 90° C. in sample buffer, resolved on a 4–20% SDS polyacrylamide gel (Novex) and visualized by silver staining. The eluate of Rse-IgG affinity purified Rse-L was reduced with 25 mM DTT prior to electrophoresis.

The Rse-L preparation was separated by SDS-PAGE under reducing conditions, electroblotted and sequenced. Electroblotting onto Millipore Immobilon PSQ membranes was carried out for 1 h at 250 mA constant current in a Biorad transblot transfer cell as described (P. Matsudaira, J. Biol. Chem. 262:10035 [1987]). The membrane was stained with 0.1% Coomassie Blue R-250 in 50% methanol for 30 sec, destained with 10% acetic acid in 50% methanol for 2 to 3 min, thoroughly washed with distilled water, dried, and stored at 4° C. Automated protein sequencing was performed on models 473A and 490A Applied Biosystems Sequencers equipped with on-line PTH analyzers. Peaks were integrated with Justice Innovation software using Nelson Analytical 760 interfaces. Sequence interpretation was performed as described (Henzel et al. J. Chromatogr. 404:41 [1987]).

The preparation gave an amino-terminal sequence of XQVLIRRXRANTL [SEQ ID NO: 8], corresponding to that of bovine protein S. Protein S sequences were obtained from several independent preparations of Rse-L. After SDS-PAGE, some preparations were characterized by the presence of a 14 kDa species having an N-terminal sequence of ANTL [SEQ ID NO: 9], as previously reported for bovine protein S, along with 60–70 kDa species with sequences corresponding to cleavage within the thrombin sensitive loop region of bovine protein S. After CnBr cleavage of the sequencing filter >99% of all identifiable residues were accounted for by a mixture of protein S CnBr fragments. Furthermore, Rse-L activity could not be separated from protein S by anion exchange chromatography in the presence of $Ca^{2+}$, cation exchange chromatography, hydrophobic interaction chromatography, Blue Sepharose chromatography, or nondenaturing gel electrophoresis. The Rse-L activity present in FBS and purified fractions could be neutralized by protein S polyclonal antisera.

Human serum or recombinant human protein S expressed in 293 cells showed low activity in either the KIRA or Rse-IgG binding assays. Human serum was obtained from Pierce and from local blood banks. Human protein S (Calbiochem, Enzyme Research Labs, or Celsus labs) had an $EC_{50}$ of >250 nM in the membrane binding assay. In comparison, the purified bovine protein S had an $EC_{50}$ of 1.2 nM in this assay. In the KIRA assay, concentrations as high as 150 nM human protein S resulted in low phosphorylation of Rse. Human protein S cDNAs were obtained by PCR using 1 µg of human fetal liver cDNA (Clontech) as template with Pfu DNA polymerase (Stratagene) as described in Mark et al. (1992), supra. Human protein S was expressed in 293 cells grown in the presence of 2 µg/ml Vitamin K exactly as described below for human gas6, and expression was verified by metabolic labeling of cultures and/or by western blotting with a polyclonal anti-protein S antiserum. Purified human protein S bound $^{125}$I-Rse-IgG, but with ~200 fold lower affinity than purified bovine protein S.

It was hypothesized that a homologue of protein S might be more effective. A search of the GENBANK data base revealed substantial similarity (44% amino acid identity, and a similar domain structure) between the amino acid sequence of human protein S and the predicted product of human growth arrest specific gene 6 (gas6) (Manfioletti et al., supra).

EXAMPLE 6

Recombinant Production of gas6

It was determined whether human gas6 was a ligand for Rse. Gas6 cDNA clones were obtained by polymerase chain reaction cloning from reverse transcribed human brain cDNA. The full-length human gas6 clone was constructed by linking together cDNAs encoding amino acids 1–318 and 319–678. Gas6 cDNAs were obtained by PCR using 1 µg of human fetal brain cDNA (Clontech) as template with Pfu DNA polymerase as described (Mark et al., *J. Biol. Chem.* 267:26166 [1992]). Forward and reverse primers designed to obtain the 5' and 3' portions of hgas6 were:

(5'-GATATCGATCCATGGCCCCTTCGCTCTC [SEQ ID NO: 10];

5'-CATGGATCCTACCGGAAGTCAAACTCAGCTA [SEQ ID NO: 11]) and (5'-GATATCGATGAGTGTGAAGTCCTTGTAC [SEQ ID NO: 12];

5'-GTCGGATCCGACAGAGACTGAGAAGCC [SEQ ID NO: 13]), respectively.

Human fetal kidney 293 cells were transiently transfected as described in Mark et al., *J. Biol. Chem.* 267:26166 (1992). After a 4 h incubation, the media was replaced with growth media plus antibiotics and 2 µg/ml Vitamin K. Conditions for metabolic labeling with $^{35}$S-Cys and $^{35}$S-Met were as described in Mark et al. For precipitation with IgG-fusion proteins, radiolabeled supernatants were first precleared with pansorbin (Calbiochem) for 30 min at room temperature, then incubated with 10 µg of the IgG fusion protein for 4 h at 4° C. Fusion proteins were precipitated with 20 µl of pansorbin, the complexes were collected by centrifugation at 14,000×g for 1 min, and then washed 3 times with PBS containing 0.1% Triton-X 100. Precipitates were analyzed by SDS-PAGE under reducing conditions (Capon et al., *Nature* 337:525 [1989]). Radioactivity in the dried gel was analyzed with a Fuji phosphoimager.

Conditioned media from cells metabolically labeled after transfection with a gas6 expression vector contained a 70 kDa protein that could be selectively precipitated by the Rse-IgG fusion protein but not by the control fusion protein CD4-IgG. Conditioned media from unlabeled transfections enhanced binding of $^{125}$I-Rse-IgG to membranes, and induced phosphorylation of Rse receptor expressed in CHO cells. These data indicated that recombinant human gas6 binds to and activates human Rse receptor.

Recombinant gas6 was purified from conditioned media by affinity chromatography. Human fetal kidney 293 cells were transiently transfected as described in Mark et al. (1992), supra. After a 4 h incubation, the media was replaced with serum free growth media plus antibiotics and 2 µg/ml Vitamin K. Conditioned media were collected at two and 4 days following transfection. The conditioned media of the transfected cells, but not those of either nontransfected or mock transfected 293 cells, activated binding of $^{125}$I-Rse-IgG. A liter of pooled conditioned media was clarified by centrifugation, diluted with 1 volume of buffer A (50 mM TrisHCl, pH 7.5, 0.1% CHAPS, 5 mM benzamidine), and applied to a 6 ml Resource Q column (Pharmacia) previously equilibrated with buffer A. The column was eluted with a 12 column volume gradient of 0 to 0.4M NaCl in buffer A. The active fractions were pooled and diluted with 1 volume buffer A and applied to a Rse-IgG affinity column that was washed and developed as described (see Example 5 above).

The identity of recombinant gas6 was verified by amino terminal sequence. The sequence of the recombinant material begins with the sequence $^{49}$AFQVFEEA$^{56}$ [SEQ ID NO: 14]. The signal from the glutamic acid residues in this sequence was weak, consistent with γ carboxylation.

Figure 5:
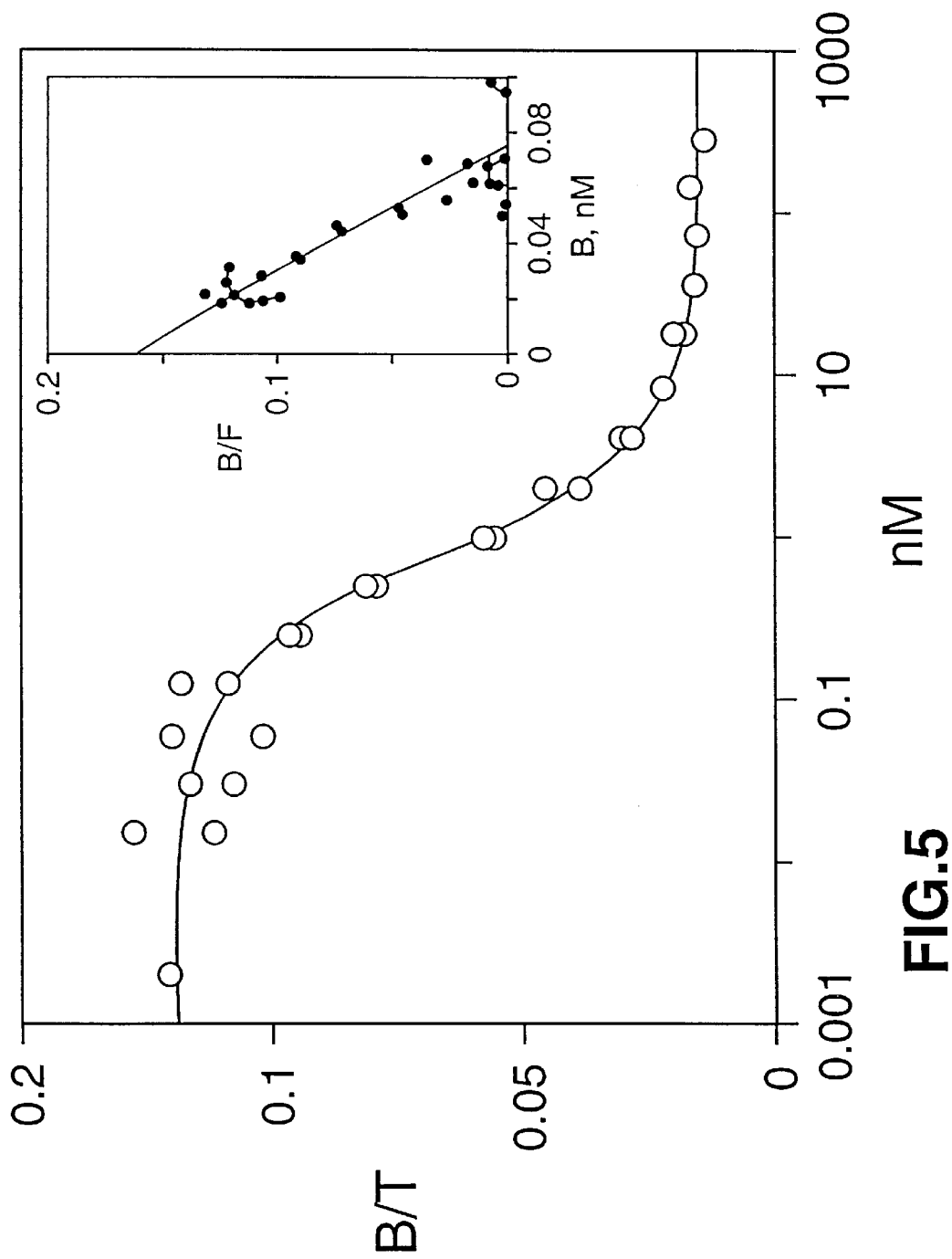
FIG. 5 displays inhibition of binding of $^{125}$I-Rse-IgG to gas6 by unlabeled Rse-IgG. Increasing amounts of unlabeled Rse-IgG were added to tubes with constant $^{125}$I-Rse-IgG and gas6. A nonlinear least squares fit to the data using a single class of sites gave an estimated equilibrium dissociation constant of 0.46±0.04 nM. The inset shows a Scatchard plot of bound (B) vs bound/free (B/F) after correction for nonspecific binding.

A well known characteristic of Gla containing proteins is their coprecipitation with insoluble barium salts (Dahlbeck, *Biochem. J.* 209:837 [1983]; Discipio and Davie, *Biochemistry* 18:899 [1979]). An assay based on this property allowed us to analyze the binding of purified gas6 to $^{125}$I-Rse-IgG in the absence of cell membranes. Samples containing various dilutions of Rse-L in 25 mM HEPES pH 7.2, 0.1% BSA and 0.05% Tween-20 were combined and mixed with $^{125}$I-Rse-IgG diluted in the same buffer in a total volume of 100–120 ml. After a 45 min incubation at room temperature, 1 ml of a freshly prepared ice cold suspension of $BaCl_2$ (10 mM) in phosphate buffered saline was added to each tube and precipitable radioactivity was collected by centrifugation and aspiration of the supernatant fluid. The dissociation constant for Rse-IgG and gas6 measured in this assay was 0.46 nM (FIG. 5).

Purified gas6 stimulated phosphorylation of Rse in a dose dependent fashion. A time course experiment showed that phosphorylation of Rse was induced within two minutes after addition of purified gas6. Activation of Rse phosphorylation by gas6 was neutralized by Rse-IgG but not by CD4-IgG.

EXAMPLE 7

Gas6 Expression and Characterization

Gas6 and Rse receptor expression in adult human brain tissues was investigated. A blot containing 2 µg of polyadenylated RNA from human brain tissues (Clontech) was hybridized with random-primed labeled probes corresponding to amino acids 1–420 of Rse or to amino acids 358–605 of gas6. The tissues were amygdala, caudate nucleus, corpus callosum, hippocampus, hypothalamus, substantia nigra, subthalamic nucleus, and thalamus.

Consistent with the hypothesis that gas6 might be a ligand for Rse, it was found that gas6 and Rse mRNA are co-expressed in each of these adult human brain tissues.

Astrocytes have been reported to synthesize neurotrophic factors that support the growth and survival of neurons. Moretto et al., *J. Neuropath & Exp Neuro.* 53:78 (1994) and Lin et al. *Science* 260: 1130 (1993). It was determined whether cultured rat astrocytes also synthesize a ligand for Rse. A northern blot was prepared which contaned 1 μg pf polyadenylated RNA from postnatal day 1 astrocytes or hippocampal neurons prepared from E18 rat embryos. Astrocytes were prepared as described (Banker and Goslin, *Culturing Nerve Cells* [MIT Press, Cambridge,1991], pp 260–261) and then cultured in serum-free media for 1 day, 3 days, or 5 days. Hippocampal neurons were cultured in serum free defined media for 0 days, 3 days or 4 days. The blot was hybridized with a $^{32}$P-labeled probe corresponding to amino acids 1–460 of murine gas6. The blot was stripped then hybridized with a $^{32}$P-labeled actin probe to confrim the integrity of the RNA samples.

Gas6 mRNA was detected in cultured type 1 astrocytes prepared from postnatal day 1 rats, but could not be detected in E18 hippocampal neurons.

Expression data for gas6 and Rse obtained herein and elsewhere is summarized in the following table.

TABLE 3

Expression of Gas6 and Rse in Primary Cell Culture and Cell Lines

| Cell Culture | Gas6 | Rse |
| --- | --- | --- |
| Neuronal System | | |
| Astrocyte | + | + |
| Hippocampus neurons | − | Schulz et al., supra |
| P45 Schwann's Neuroglioma | − | + |
| G28 | + | − |
| G59 | + | − |
| G111 | + | − |
| Glioblastoma, astrocytorum | | |
| U87MG | − | − |
| U373MG | + | − |
| Hematopoietic System | | |
| JM, a CML line | n/a | + |
| CMK11-5 | n/a | + |
| Jurkat | n/a | + |
| NIH3T3 | + | + |
| 293 | + | − |

Figure 6C:
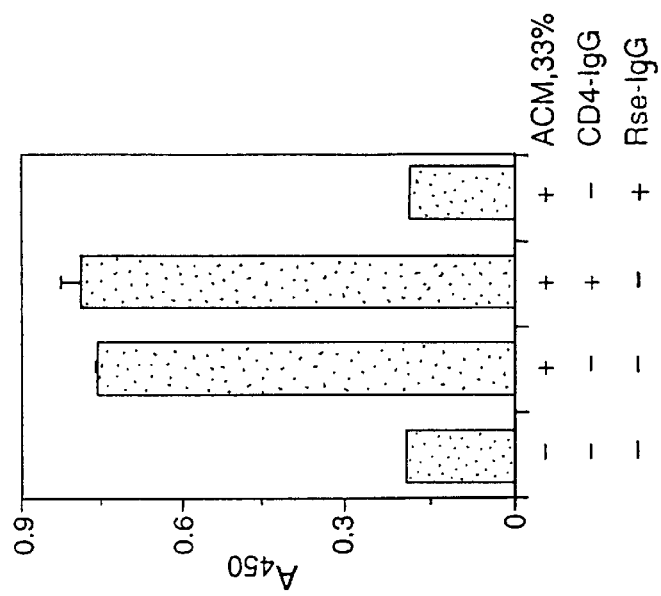
FIGS. 6A–6C show Rse-L activity in astrocyte cultures. To determine if astrocytes secrete Rse ligand, serum free media that was conditioned for 3 days was concentrated 10-fold in a Centricon-10 centrifugal ultrafiltration device, and added directly to assay tubes to give the final concentrations indicated.
Figure 6B:
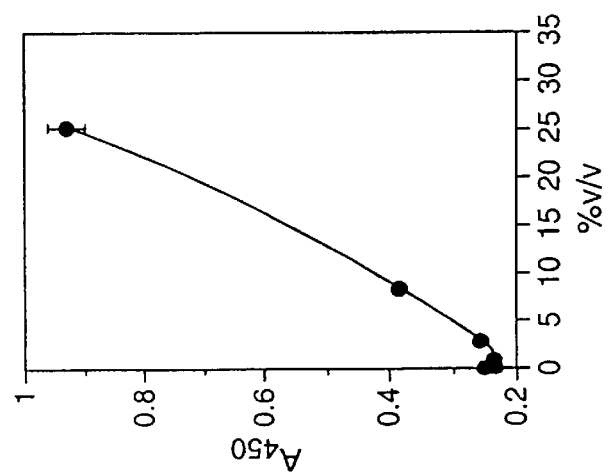
Figure 6A:
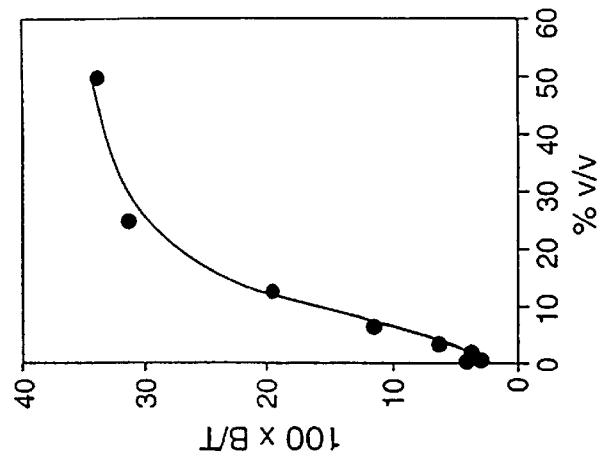

The ability of cultured rat astrocytes to also synthesize a ligand for the Rse receptor was investigated. See figure legends for FIGS. 6A–6C. Astrocyte conditioned media contained a factor which bound $^{125}$I-Rse-IgG (FIG. 6A) and stimulated tyrosine phosphorylation of Rse (FIG. 6B). This activity was neutralized by Rse-IgG but not CD4-IgG (FIG. 6C).

EXAMPLE 8

Gas6 Variants

To further characterize the interactions of gas6 with cell membranes and with Rse, a series of N-terminal deletion variants containing an epitope tag were constructed.

Figure 7:
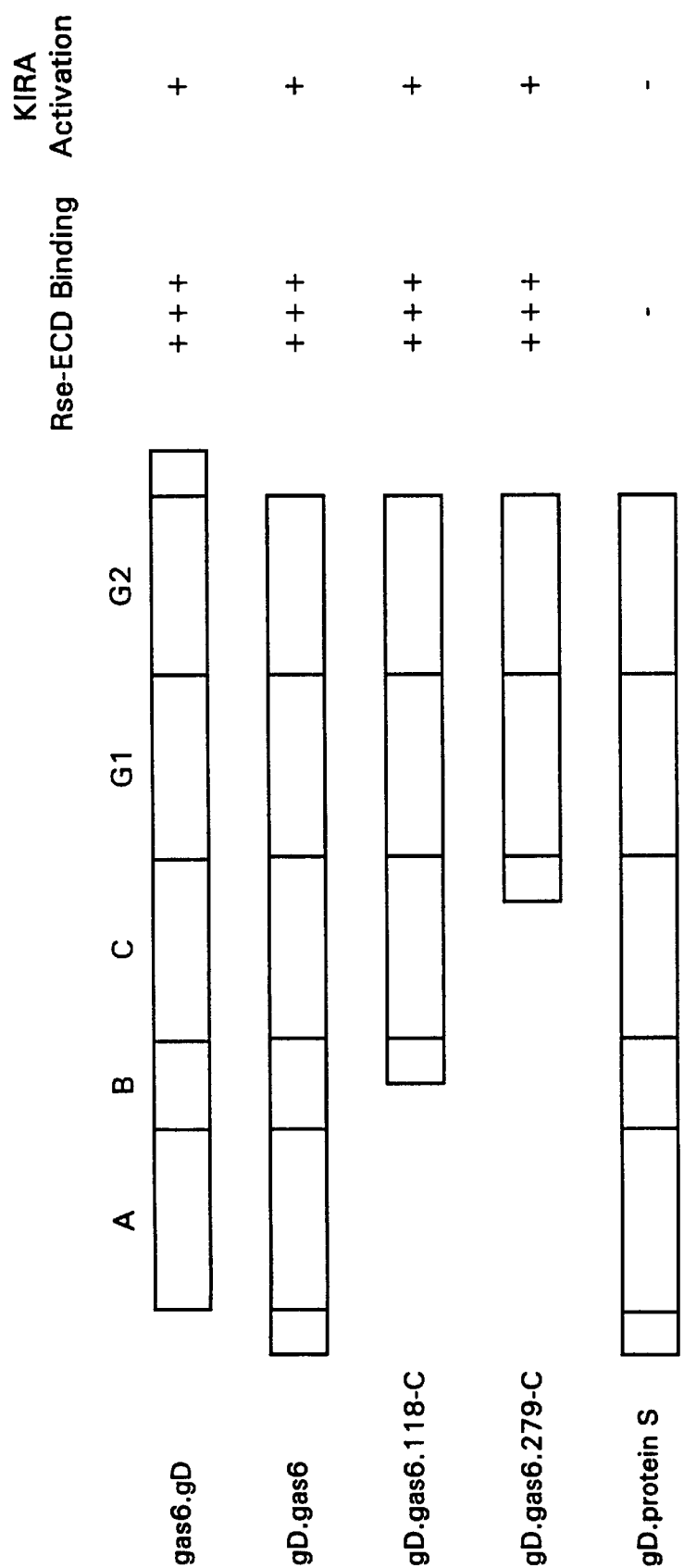
As shown in FIG. 7, a deletion analysis of gas6 indicated that the G domains are sufficient for binding to Rse in vitro. Epitope tagged (gD) gas6 or protein S, or N-terminal truncation variants of gas6 (containing the indicated residues) were constructed and transiently expressed in 293 cells essentially following the procedure described in Example 6. Proteins of the correct molecular weight could be detected in unfractionated (input) cell supernatants using an antibody directed against the epitope tag. In contrast to protein S, the gas6 derivatives were precipitated from the cell supernatants by Rse-IgG. The binding was specific to the extracellular domain of Rse because proteins were not precipitated by control human Fc. For quantification purposes, the unfractionated (input) lanes represented 20% of the material used for precipitation.

The coding sequences for the gD signal sequence and epitope tag (Mark et al., [1992] supra) were fused via an Xhol site that was added by PCR to coding sequences immediatetly before the first amino acid of mature gas6 (gD.gas6; forward primer 5'-AGCTGCTCGAGGCGCTGTTGCCGGCGC [SEQ ID NO: 15]) or protein S (gD.protein S; forward primer 5'-AGCTGCTCGAGGCAAATTCTTTACTTGAA[SEQ ID NO: 16], or amino acids 118 (gD.gas6.118-C; forward primer 5'-AGCTGCTCGAGGACCAGTGCACGCCCAACC [SEQ ID NO: 17]) and 279 (gD.gas6.279-C; forward primers 5'- GCTGCTCGAGGACATCTTGCCGTGCGTG [SEQ ID NO: 18]) of gas6. The reverse primer for gD.gas6 and gD.gas6.118-C was 5'-CATGGATCCTACCGGAAGTCAAACTCAGCTA [SEQ ID NO: 11]. The reverse primers for gD.gas6.279-C and gD.protein S were 5'-GTCGGATCCGACAGAGACTGAGAAGCC [SEQ ID NO: 13] and 5'-CATTCATTTATGTCAAATTCA[SEQ ID NO: 19], respectively. Gas6.gD was constructed by fusing the coding sequences of gas6 to the C-terminal gD tag used for Rse.gD through an Nhel site which was added by PCR using the primers 5'-ATGGAGATCAAGGTCTG [SEQ ID NO: 20] and 5'-CATCTTGAGGCTAGCGGCTGCGGCGGGCTCCAC [SEQ ID NO: 21]. The polypeptides were expressed in 293 cells using the procedure essentially as described for full length gas6 in Example 6.

gD.gas6.118-C and gD.gas6.279-C, containing the EGF repeats and tandem G domains within the D domain, or just the G domains, respectively, were precipitated by Rse-IgG (FIG. 7) from cell culture supernatants. Human protein S was not precipitated in this assay which is consistent with the above observations that human protein S binds Rse with a lower affinity than human gas6. These derivatives of gas6 that were truncated for the Gla domain (i.e. the A domain) also fail to associate with membranes in a $Ca^{2+}$ fashion.

This data shows that gas6 binds to Rse through the G domains, that the membrane binding and Rse-binding activities are separable, and suggests that the Gla domain is required for $Ca^{2+}$ dependent association with cell membranes.

The gas6 variants described in this example were functionally active. In particular, gD.gas6.118-C and gD.gas6.279-C activated Rse phosphorylation in the KIRA assay described in Example 4 as effectively as full-length gD-tagged gas6 (see FIG. 7).

EXAMPLE 9

Cell Proliferation Assay

Figure 8:
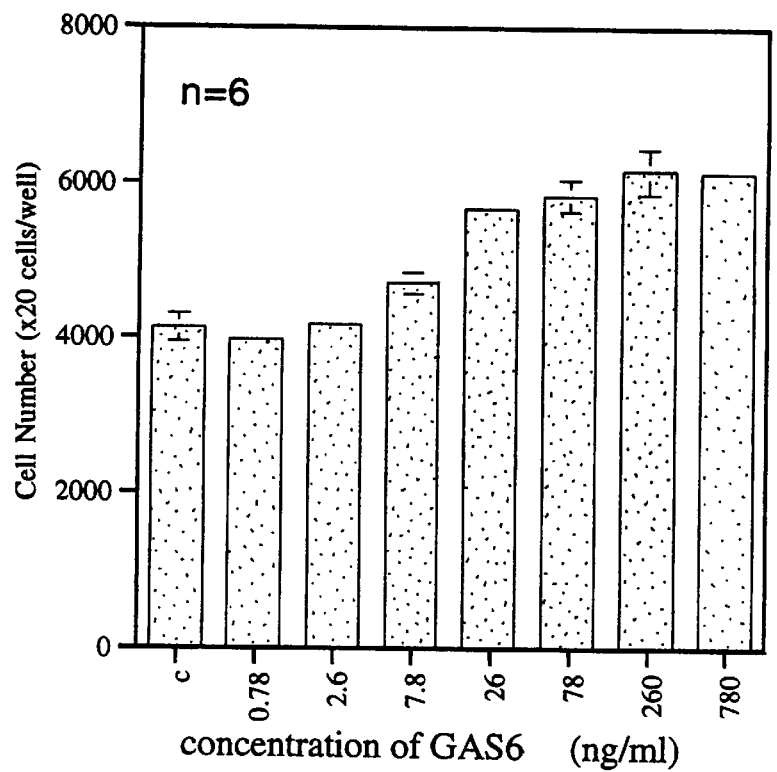
FIG. 8 shows that gas6 induces the proliferation of P45 rat Schwann cells in a dose responsive fashion. Cells were plated in 24-well plates in F 12/DME medium with 10 μg/ml insulin and transferrin and 5 μg/ml Vitamin E with the indicated concentrations of recombinant human gas6. Cells were counted with a Coulter counter after 48 h. The mean and standard deviation for six wells for each treatment are shown.
Figure 9:
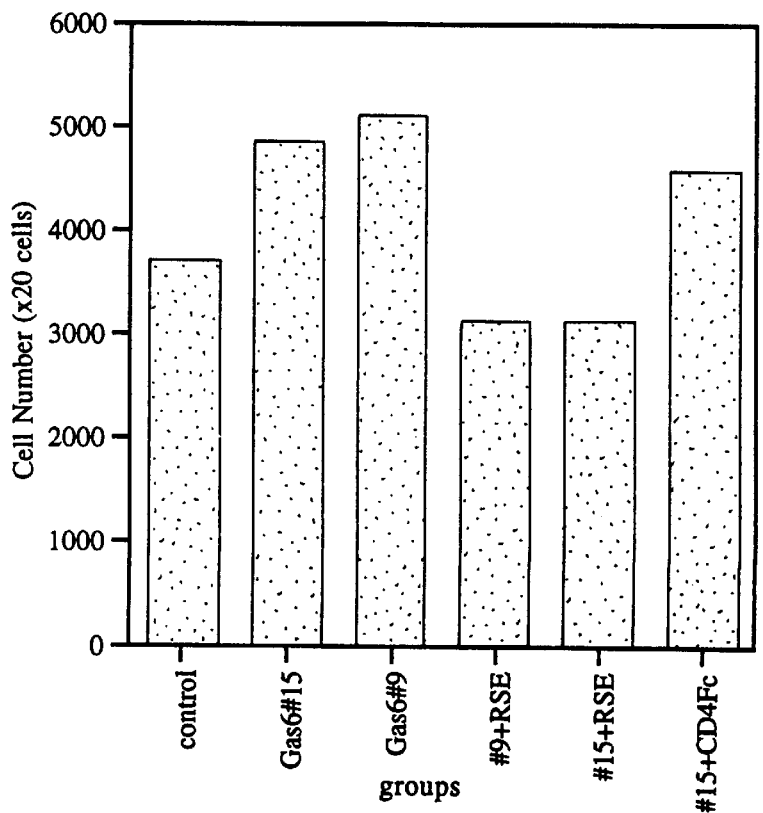
FIG. 9 illustrates that gas6 induced proliferation of p45 rat Schwann cells is neutralized by Rse-IgG. Cells were plated as described in FIG. 8 legend. Control cells received no further additions. All other cells were treated with two different purifications of gas6 (i.e. lot #15 and lot #9) and 10 μg/ml of either Rse-IgG (labeled Rse) or CD4-IgG (labeled CD4Fc).

Rse mRNA, but not gas6 mRNA was also detected in the rat Schwann cell line P45, which is derived form rat E14 dorsal root ganglia. Addition of purified gas6 to these cells resulted in a dose dependent increase in cell number (50% increase at 48 hours) with an $EC_{50}$ of ~0.3 nM (FIG. 8). Gas6 treatment also altered the morphology of these cells; untreated cells were multipolar with numerous branched processes whereas gas6 treated cells became spindle-shaped with two major smooth processes and aligned themselves in a parallel array. It was also demonstrated that gas6-induced proliferation was neutralized by Rse-IgG but not CD4-IgG. See FIG. 9.

It is beneficial to have populations of mammalian Schwann cells (preferably human Schwann cells) for use as cellular prostheses for transplantation into areas of damaged spinal cord in an effort to influence regeneration of interrupted central axons, for assisting in the repair of peripheral nerve injuries and as alternatives to multiple autografts. See Levi et al., *J. Neuroscience* 14(3):1309–1319 (1994). The use of cell culture techniques to obtain an abundant source of autologous graft material from a small biopsy has already met with clinical success in providing human epidermal cells to cover extensive burns (Gallico et al., *N. Eng J. Med.*, 311:338–451 [1984]). Furthermore, it has been shown that Schwann cells from human xenografts are capable of myelinating regenerating peripheral axons from mice which have been immunosuppressed (Aguayo et al., *Nature* 268:753–755[1977], and Aguayo et al., *Soc. Neurosci. Symp.* 4:361–383 [1979]). Accordingly, it is expected that the above approach will meet with success in mammals, including humans.

In order to generate such populations of glial cells, mammalian (e.g. human) peripheral nerves are obtained from donors. The nerves are harvested within 30 min of aortic clamping and stored in RPMI (GIBCO Laboratories, Grand Island, N.Y.) at 4° C. for not more than 24 hours. Each peripheral nerve is prepared for culture according to the protocol of Morrissey et al., *J. Neurosci* 11:2433–2442 (1991). This includes washing the nerve three times in Lebovitz's L15 (GIBCO), stripping the epineurium of the nerve, and removing individual fascicles from the remaining interfascicular epineurium. The fascicles are cut into explants 2–4 mm long and placed in 35 mm culture dishes. The prepared nerves are kept in a humidified atmosphere with 5% $CO_2$ and the medium is replaced twice per week with Dulbecco's Modified Eagle's Medium (DMEM; GIBCO) with 10% fetal calf serum (FCS). The individual explants are transplanted to new dishes after a confluent nomolayer of predominantly fibroblasts (Fbs) has been generated as an outgrowth.

After one to three transplantations the nerve explants are dissociated according to the protocol of Pleasure et al., *Ann. N.Y. Acad. Sci.* 486:227–240 (1986). In brief, multiple explants are pooled and placed in 1–2 ml of an enzyme cocktail consisting of 1.25 U/ml dispase (Boehringer Mannheim Biochemicals, Germany), 0.05% collagenase (Worthington Biochemicals Corp., Freehold, N.J.) and 15.% FCS in DMEM. The explants are left in enzymes overnight and gently triturated the following morning with a straight glass borosilicate pipette, until individual explants can no longer be recognized. The cells are then washed in L15 and 10% FCS and plated on 100 mm culture dishes coated with 200 μm/ml poly-L-lysine (PLL; Sigma, St. Louis, Mo.).

The following day the cells are taken off the PLL-coated culture plates by rinsing twice with $Ca^{2+}$ and $Mg^{2+}$-free Hanks Balanced Salt Solution (HBSS; GIBCO) and exposing them to trypsin (0.05%) and EDTA (0.02%)(Sigma) in HBSS for 5–10 min at 37° C. The cells are collected and rinsed twice in L15 and 10% FCS, counted on a hemocytometer, and then diluted into a calculated volume of DMEM and 10% FCS (D10). The cells are then seeded on an Aclar (Allied Fiber and Plastics, Pottsville, Penna.) mini dishes coated with ammoniated collagen or PLL-coated culture dishes are then seeded on PLL-coated dishes and exposed to media containing D10 with gas6 (e.g. 10 nM) cholera toxin (CT) Sigma, St. Louis, Mo. (100 ng/ml), and forskolin (1 μM) Sigma. The medium is changed three times per week and when the cells have reached confluency, they are taken up from the culture dishes with trypsin (0.05%)/EDTA(0.02%) solution.

The cells which are thus generated in cell culture are then surgically placed in patients.

EXAMPLE 10

Gas6 Immunoadhesin gD.gas6.279-C.IgG was constructed by fusing the coding sequences of gD.gas6.279-C (see Example 8) to amino acids 216–443 of human IgGγ1 through a BstEII linker (adding amino acids Val and Thr). The linker was added to gD.gas6.279-C sequences by PCR using the primers 5'-ATGGAGATCAAGGTCTG [SEQ ID NO: 20] and 5'-GTCGGTGACCGCTGCTGCGGGCTCCAC [SEQ ID NO: 22].

Figure 10:
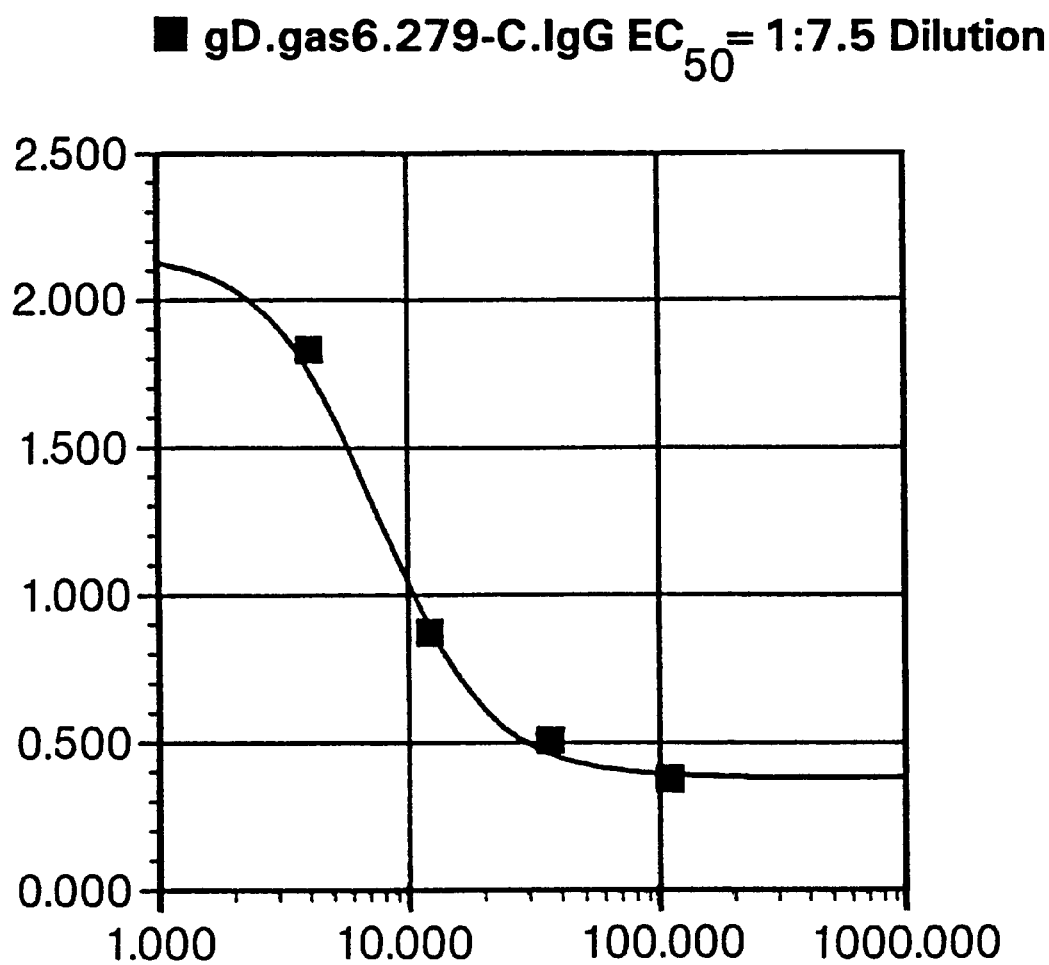
FIG. 10 shows a dose response curve for activation of Rse phosphorylation in the KIRA assay as described in Example 10.

The gas6 immunoadhesin thus formed was subjected to the KIRA assay described in Example 4 above. Briefly, different dilutions of conditioned media from cells transiently expressing gD.gas6.279-C.IgG were tested in the KIRA assay. The starting material had a concentration of gD.gas6.279-C.IgG of ~230 ng/ml. The $EC_{50}$ for activation was approximately 0.4 nM. See FIG. 10. Activity was not observed in conditioned media from transiently transfected control cell lines.

EXAMPLE 11

Activation of Rse by Non-γ Carboxylated Gas6

Media (700 ml) conditioned for 3 days by 293 cells transfected with human gas6 (hgas6.17) was dialyzed against 2×8 L of 50 mM Tris-HCl pH 7.5, 5 mM benzamidine (buffer A). The dialyzate was adjusted to 0.1% CHAPS, and loaded on a 6 ml Resource-Q column (Pharmacia) at 10 ml/minute. The column was washed with buffer A, and eluted with a 70 ml linear gradient of 0 to 0.4M NaCl in buffer A, at a flow rate of 1.0 ml/min, collecting fractions of 2.0 ml.

The fractions were analyzed for their ability to bind and activate Rse using the barium chloride binding method described in Example 6 and the KIRA assay described in Example 4. The barium chloride assay can only detect binding of Gla containing Rse ligands, while the KIRA assay is sensitive to all Rse activators. Binding activity was centered at fraction 31, while KIRA showed an additional earlier eluting peak centered at fraction 24.

Aliquots (10 μl) of fractions 20 to 44 were analyzed on 8% acrylamide (Novex) SDS gels, and proteins visualized by silver staining. In these fractions a 75 kD band comigrated with standard hgas6. Integrated intensities of the 75 kD band were measured by laser scanning (Molecular Dynamics) and image analysis (NIH Image). Peak intensities were found in fractions 24 and 31, corresponded to the 2 regions of KIRA activity. The amount of hgas6 in each fraction was estimated from the staining intensity of a known quantity (0.34 μg) of a standard preparation of hgas6 run on the same gel, assuming a linear relationship between staining intensity and protein load.

Sequence analysis of the 75 kD bands from fractions 24 and 31 was performed after SDS-PAGE and electrophoretic transfer to PVDF membranes. The amino terminal sequence of both bands was unambiguously identified as that of hgas6 (AFQVF), but the two could be differentiated by the presence or absence of modified glutamic acid residues in later cycles. The sequence from fraction 31 lacked a signal from glutamic acid in cycles 6,7,14, and 16, consistent with a γ-carboxyl modification of these residues. The sequence from fraction 24 was consistent with unmodified glutamic acid at all these positions.

Figure 11:
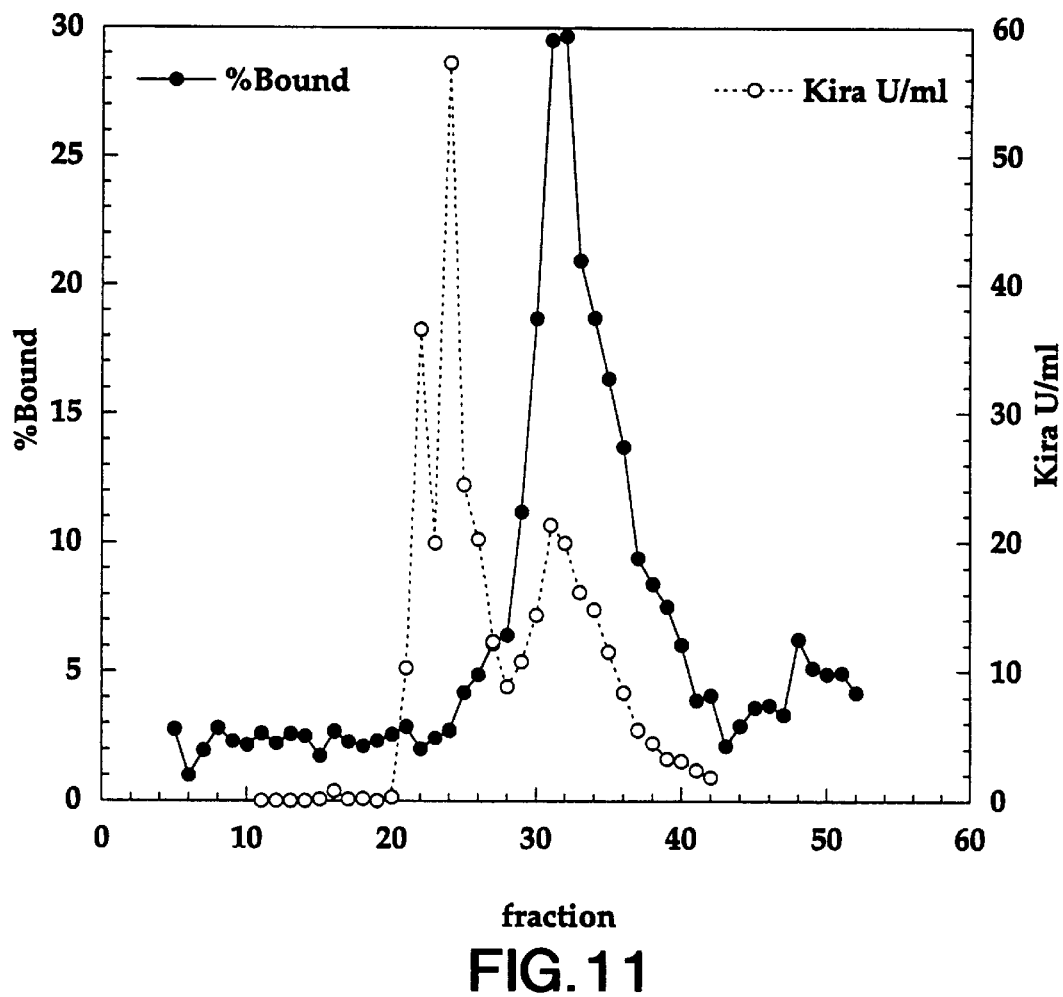
FIG. 11 illustrates ion exchange chromatography of media conditioned by cells expressing human recombinant gas6. Media (700 ml) was dialyzed against buffer A (50 mM Tris-HCl pH 7.5, 5 mM benzamidine), adjusted to 0.1% CHAPS, and loaded on a 6 ml Resource-Q column (Pharmacia) at 10 ml/minute. The column was washed with buffer A, and eluted with a 70 ml linear gradient of 0 to 0.4M NaCl in buffer A at a flow rate of 1.0 ml/min collecting fractions of 2.0 ml. The fractions were analyzed for their ability to bind and activate Rse using the barium chloride binding method described in Example 6 and the KIRA assay described in Example 4. The binding activity is expressed as the percent of total radioactivity added which is precipitated by barium chloride. The KIRA activity is expressed in units/ml relative to a standard.

Both sequence analysis and binding behavior of the early eluting form of hgas6 are consistent with its identification as an unmodified form of hgas6, lacking the characteristic γ-carboxyl modification of glutamic acid. This second discovered form of recombinant hgas6 appears to be more active than the first described Gla containing form. The specific activity of the two forms was calculated from the KIRA data in FIG. 11 and from the densitometric quantitation of hgas6. The specific activity of fraction 31 (form 1 is 1170 KIRA units/mg P, while that of fraction 24 (form 2) is 3158. This indicates that form 2, lacking the Gla modification, is more potent than the Gla containing form 1 in activating Rse.

What is claimed is:

1. A composition comprising variant gas6 which lacks one or more glutamic acid residues from the A domain of a native gas6 and a pharmaceutically acceptable carrier, wherein said variant gas6 maintains a functional activity of a native gas6, and wherein said functional activity is Rse receptor activation.

2. The composition of claim 1, wherein the variant gas6 is less γ-carboxylated than native gas6.

3. The composition of claim 1, wherein the variant gas6 lacks the A domain of native gas6.

4. The composition of claim 1, wherein the variant gas6 is derived from human gas6.

5. The composition of claim 1, wherein the pharmaceutically acceptable carrier is selected from the group consisting of a buffer, antioxidant, low molecular weight polypeptide having less than about 10 residues, protein, amino acid, hydrophilic polymer, carbohydrate, chelating agent, sugar alcohol, salt-forming counterion and non-ionic surfactant.

6. The composition of claim 1 further comprising a neurotropic factor.

7. The composition of claim 6, wherein the neurotropic factor is selected from the group consisting of nerve growth factor (NGF), neurotropin, bone derived nerve factor (BDNF) and insulin-like growth factor.

8. The composition of claim 1 which is sterile.

9. The composition of claim 1 which is lyophilized.

10. A container having a sterile access port in which is contained the composition of claim 1.

11. The container of claim 10 which is an intravenous solution bag or vial having a stopper pierceable by a hypodermic injection needle.

12. The composition of claim 1 which is a sustained-release formulation.

13. A liposome comprising the gas6 composition of claim 1.

14. An article of manufacture, comprising:
a container,
a label on said container, and
a composition contained within said container, wherein the composition is the composition of claim 1.

15. A kit, comprising:
a first container,
a label on said container,
a composition contained within said container, wherein the composition is the composition of claim 1, and
a second container comprising a buffer.

16. A composition comprising variant gas6 in an amount effective for activating the Rse receptor and a pharmaceutically acceptable carrier, wherein said variant gas6 consists of the D domain of gas6.

17. A composition comprising variant gas6 in an amount effective for activating the Rse receptor and a pharmaceutically acceptable carrier, wherein said variant gas6 consists of a G domain of gas6.

18. The composition of claim 16 or 17, wherein said gas6 domain is from human gas6.

19. The composition of claim 16 or 17, wherein the pharmaceutically acceptable carrier is selected from the group consisting of a buffer, antioxidant, low molecular weight polypeptide having less than about 10 residues, protein, amino acid, hydrophilic polymer, carbohydrate, chelating agent, sugar alcohol, salt-forming counterion and non-ionic surfactant.

20. The composition of claim 16 or 17 further comprising a neurotropic factor.

21. The composition of claim 20, wherein the neurotropic factor is selected from the group consisting of nerve growth factor (NGF), neurotropin, bone derived nerve factor (BDNF) and insulin-like growth factor.

22. The composition of claim 16 or 17 which is sterile.

23. The composition of claim 16 or 17 which is lyophilized.

24. A container having a sterile access port in which is contained the composition of claim 16 or 17.

25. The container of claim 24 which is an intravenous solution bag or vial having a stopper pierceable by a hypodermic injection needle.

26. The composition of claim 16 or 17 which is a sustained-release formulation.

27. A liposome comprising the gas6 composition of claim 16 or 17.

28. An article of manufacture, comprising:
a container,
a label on said container, and
a composition contained within said container, wherein the composition is the composition of claim 16 or 17.

29. A kit, comprising:
a first container,
a label on said container,
a composition contained within said container, wherein the composition is the composition of claim 16 or 17, and
a second container comprising a buffer.

30. A variant gas6 which lacks one or more glutamic acid residues from the A domain of native gas6 adsorbed onto a membrane which can be implanted in proximity to damaged neural tissue, wherein said variant gas6 activates the Rse receptor.

31. A composition comprising gas6 admixed with a polypeptide selected from the group consisting of nerve growth factor, a neurotropin, insulin, insulin-like growth factor-1, insulin-like growth factor-2 and bone derived nerve factor, wherein said gas6 is variant gas6 which lacks one or more glutamic acid residues from the A domain of native gas6 and wherein said variant gas6 activates the Rse receptor.

* * * * *

UNITED STATES PATENT AND TRADEMARK OFFICE
CERTIFICATE OF CORRECTION

PATENT NO. : 6,211,142 B1
DATED : April 3, 2001
INVENTOR(S) : Hammonds et al.

It is certified that error appears in the above-identified patent and that said Letters Patent is hereby corrected as shown below:

Column 1,
Line 19, delete "Mark et al." and insert therefor -- Mark et al., --.

Column 2,
Line 3, delete "Rescigno et al." and insert therefor -- Rescigno et al., --
Line 3, delete "Bellosta et al." and insert therefor -- Bellosta et al., --
Line 22, delete "Manfioletti et al." and insert therefor -- Manfioletti et al., --
Line 26, delete "Colombo et al." and insert therefor -- Colombo et al., --
Line 27, delete "Ferrero et al." and insert therefor -- Ferrero et al., --
Line 34, delete "Easmon et al." and insert therefor -- Easmon et al., --
Line 44, delete "cascade." and insert therefor -- cascade --
Line 46, delete "reported." and insert therefor -- reported --

Column 27,
Line 27, delete "warfarin" and insert therefor -- warfarin. --

Column 34,
Line 59, delete "37 °C." and insert therefor -- 37 °C --.
Line 67, delete "37 °C." and insert therefor -- 37 °C --.

Column 35,
Line 17, delete "4 °C." and insert therefor -- 4°C --.

Column 36,
Line 41, delete "90 °C." and insert therefor -- 90 °C --.,
Line 54, delete "4 °C." and insert therefor -- 4 °C --.

Column 38,
Line 4, delete "4 °C." and insert therefor -- 4 °C --.

UNITED STATES PATENT AND TRADEMARK OFFICE
CERTIFICATE OF CORRECTION

PATENT NO. : 6,211,142 B1
DATED : April 3, 2001
INVENTOR(S) : Hammonds et al.

It is certified that error appears in the above-identified patent and that said Letters Patent is hereby corrected as shown below:

Column 39,
Line 12, delete "Lin et al." and insert therefor -- Lin et al., --.

Column 41,
Line 21, delete "4 °C." and insert therefor -- 4 °C --.
Line 42, delete "15.%" and insert therefor -- 15% --.

Signed and Sealed this

Sixteenth Day of October, 2001

Attest:

*Attesting Officer*

NICHOLAS P. GODICI
*Acting Director of the United States Patent and Trademark Office*

```
                          SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 673 amino acids
        (B) TYPE: amino acid
        (D) TOPOLOGY: linear (xi) SEQUENCE DESCRIPTION: SEQ ID NO:1:

Met Pro Pro Pro Gly Pro Ala Ala Ala Leu Gly Thr Ala Leu
     1               5                  10                  15

Leu Leu Leu Leu Leu Ala Ser Glu Ser Ser His Thr Val Leu Leu
                        20                  25                  30

Arg Ala Arg Glu Ala Ala Gln Phe Leu Arg Pro Arg Gln Arg Arg
                        35                  40                  45

Ala Tyr Gln Val Phe Glu Glu Ala Lys Gln Gly His Leu Glu Arg
                        50                  55                  60

Glu Cys Val Glu Glu Val Cys Ser Lys Glu Glu Ala Arg Glu Val
                        65                  70                  75

Phe Glu Asn Asp Pro Glu Thr Glu Tyr Phe Tyr Pro Arg Tyr Gln
                        80                  85                  90

Glu Cys Met Arg Lys Tyr Gly Arg Pro Glu Glu Lys Asn Pro Asp
                        95                 100                 105

Phe Ala Lys Cys Val Gln Asn Leu Pro Asp Gln Cys Thr Pro Asn
                       110                 115                 120

Pro Cys Asp Lys Lys Gly Thr His Ile Cys Gln Asp Leu Met Gly
                       125                 130                 135

Asn Phe Phe Cys Val Cys Thr Asp Gly Trp Gly Gly Arg Leu Cys
                       140                 145                 150

Asp Lys Asp Val Asn Glu Cys Val Gln Lys Asn Gly Gly Cys Ser
                       155                 160                 165

Gln Val Cys His Asn Lys Pro Gly Ser Phe Gln Cys Ala Cys His
                       170                 175                 180

Ser Gly Phe Ser Leu Ala Ser Asp Gly Gln Thr Cys Gln Asp Ile
                       185                 190                 195

Asp Glu Cys Thr Asp Ser Asp Thr Cys Gly Asp Ala Arg Cys Lys
                       200                 205                 210

Asn Leu Pro Gly Ser Tyr Ser Cys Leu Cys Asp Glu Gly Tyr Thr
                       215                 220                 225

Tyr Ser Ser Lys Glu Lys Thr Cys Gln Asp Val Asp Glu Cys Gln
                       230                 235                 240

Gln Asp Arg Cys Glu Gln Thr Cys Val Asn Ser Pro Gly Ser Tyr
                       245                 250                 255

Thr Cys His Cys Asp Gly Arg Gly Gly Leu Lys Leu Ser Pro Asp
                       260                 265                 270

Met Asp Thr Cys Glu Asp Ile Leu Pro Cys Val Pro Phe Ser Met
```

-continued

```
                275                 280                 285
Ala Lys Ser Val Lys Ser Leu Tyr Leu Gly Arg Met Phe Ser Gly
                290                 295                 300

Thr Pro Val Ile Arg Leu Arg Phe Lys Arg Leu Gln Pro Thr Arg
            305                 310                 315

Leu Leu Ala Glu Phe Asp Phe Arg Thr Phe Asp Pro Glu Gly Val
        320                 325                 330

Leu Phe Phe Ala Gly Gly Arg Ser Asp Ser Thr Trp Ile Val Leu
        335                 340                 345

Gly Leu Arg Ala Gly Arg Leu Glu Leu Gln Leu Arg Tyr Asn Gly
        350                 355                 360

Val Gly Arg Ile Thr Ser Ser Gly Pro Thr Ile Asn His Gly Met
        365                 370                 375

Trp Gln Thr Ile Ser Val Glu Glu Leu Glu Arg Asn Leu Val Ile
        380                 385                 390

Lys Val Asn Lys Asp Ala Val Met Lys Ile Ala Val Ala Gly Glu
        395                 400                 405

Leu Phe Gln Leu Glu Arg Gly Leu Tyr His Leu Asn Leu Thr Val
        410                 415                 420

Gly Gly Ile Pro Phe Lys Glu Ser Glu Leu Val Gln Pro Ile Asn
        425                 430                 435

Pro Arg Leu Asp Gly Cys Met Arg Ser Trp Asn Trp Leu Asn Gly
        440                 445                 450

Glu Asp Ser Ala Ile Gln Glu Thr Val Lys Ala Asn Thr Lys Met
        455                 460                 465

Gln Cys Phe Ser Val Thr Glu Arg Gly Ser Phe Phe Pro Gly Asn
        470                 475                 480

Gly Phe Ala Thr Tyr Arg Leu Asn Tyr Thr Arg Thr Ser Leu Asp
        485                 490                 495

Val Gly Thr Glu Thr Thr Trp Glu Val Lys Val Val Ala Arg Ile
        500                 505                 510

Arg Pro Ala Thr Asp Thr Gly Val Leu Leu Ala Leu Val Gly Asp
        515                 520                 525

Asp Asp Val Val Ile Ser Val Ala Leu Val Asp Tyr His Ser Thr
        530                 535                 540

Lys Lys Leu Lys Lys Gln Leu Val Val Leu Ala Val Glu Asp Val
        545                 550                 555

Ala Leu Ala Leu Met Glu Ile Lys Val Cys Asp Ser Gln Glu His
        560                 565                 570

Thr Val Thr Val Ser Leu Arg Glu Gly Glu Ala Thr Leu Glu Val
        575                 580                 585

Asp Gly Thr Lys Gly Gln Ser Glu Val Ser Thr Ala Gln Leu Gln
        590                 595                 600

Glu Arg Leu Asp Thr Leu Lys Thr His Leu Gln Gly Ser Val His
        605                 610                 615

Thr Tyr Val Gly Gly Leu Pro Glu Val Ser Val Ile Ser Ala Pro
        620                 625                 630

Val Thr Ala Phe Tyr Arg Gly Cys Met Thr Leu Glu Val Asn Gly
        635                 640                 645

Lys Ile Leu Asp Leu Asp Thr Ala Ser Tyr Lys His Ser Asp Ile
        650                 655                 660

Thr Ser His Ser Cys Pro Pro Val Glu His Ala Thr Pro
        665                 670             673
```

(2) INFORMATION FOR SEQ ID NO:2:

(i) SEQUENCE CHARACTERISTICS:
        (A) LENGTH: 678 amino acids
        (B) TYPE: amino acid
        (D) TOPOLOGY: linear (xi) SEQUENCE DESCRIPTION: SEQ ID NO:2:

```
Met Ala Pro Ser Leu Ser Pro Gly Pro Ala Ala Leu Arg Arg Ala
 1               5                  10                  15

Pro Gln Leu Leu Leu Leu Leu Ala Ala Glu Cys Ala Leu Ala
                20                  25                  30

Ala Leu Leu Pro Ala Arg Glu Ala Thr Gln Phe Leu Arg Pro Arg
                35                  40                  45

Gln Arg Arg Ala Phe Gln Val Phe Glu Glu Ala Lys Gln Gly His
                50                  55                  60

Leu Glu Arg Glu Cys Val Glu Glu Leu Cys Ser Arg Glu Glu Ala
                65                  70                  75

Arg Glu Val Phe Glu Asn Asp Pro Glu Thr Asp Tyr Phe Tyr Pro
                80                  85                  90

Arg Tyr Leu Asp Cys Ile Asn Lys Tyr Gly Ser Pro Tyr Thr Lys
                95                 100                 105

Asn Ser Gly Phe Ala Thr Cys Val Gln Asn Leu Pro Asp Gln Cys
               110                 115                 120

Thr Pro Asn Pro Cys Asp Arg Lys Gly Thr Gln Ala Cys Gln Asp
               125                 130                 135

Leu Met Gly Asn Phe Phe Cys Leu Cys Lys Ala Gly Trp Gly Gly
               140                 145                 150

Arg Leu Cys Asp Lys Asp Val Asn Glu Cys Ser Gln Glu Asn Gly
               155                 160                 165

Gly Cys Leu Gln Ile Cys His Asn Lys Pro Gly Ser Phe His Cys
               170                 175                 180

Ser Cys His Ser Gly Phe Glu Leu Ser Ser Asp Gly Arg Thr Cys
               185                 190                 195

Gln Asp Ile Asp Glu Cys Ala Asp Ser Glu Ala Cys Gly Glu Ala
               200                 205                 210

Arg Cys Lys Asn Leu Pro Gly Ser Tyr Ser Cys Leu Cys Asp Glu
               215                 220                 225

Gly Phe Ala Tyr Ser Ser Gln Glu Lys Ala Cys Arg Asp Val Asp
               230                 235                 240

Glu Cys Leu Gln Gly Arg Cys Glu Gln Val Cys Val Asn Ser Pro
               245                 250                 255

Gly Ser Tyr Thr Cys His Cys Asp Gly Arg Gly Gly Leu Lys Leu
               260                 265                 270

Ser Gln Asp Met Asp Thr Cys Glu Asp Ile Leu Pro Cys Val Pro
               275                 280                 285

Phe Ser Val Ala Lys Ser Val Lys Ser Leu Tyr Leu Gly Arg Met
               290                 295                 300

Phe Ser Gly Thr Pro Val Ile Arg Leu Arg Phe Lys Arg Leu Gln
               305                 310                 315

Pro Thr Arg Leu Val Ala Glu Phe Asp Phe Arg Thr Phe Asp Pro
               320                 325                 330

Glu Gly Ile Leu Leu Phe Ala Gly Gly His Gln Asp Ser Thr Trp
               335                 340                 345
```

```
Ile Val Leu Ala Leu Arg Ala Gly Arg Leu Glu Leu Gln Leu Arg
                350                 355                 360

Tyr Asn Gly Val Gly Arg Val Thr Ser Ser Gly Pro Val Ile Asn
                365                 370                 375

His Gly Met Trp Gln Thr Ile Ser Val Glu Glu Leu Ala Arg Asn
                380                 385                 390

Leu Val Ile Lys Val Asn Arg Asp Ala Val Met Lys Ile Ala Val
                395                 400                 405

Ala Gly Asp Leu Phe Gln Pro Glu Arg Gly Leu Tyr His Leu Asn
                410                 415                 420

Leu Thr Val Gly Gly Ile Pro Phe His Glu Lys Asp Leu Val Gln
                425                 430                 435

Pro Ile Asn Pro Arg Leu Asp Gly Cys Met Arg Ser Trp Asn Trp
                440                 445                 450

Leu Asn Gly Glu Asp Thr Thr Ile Gln Glu Thr Val Lys Val Asn
                455                 460                 465

Thr Arg Met Gln Cys Phe Ser Val Thr Glu Arg Gly Ser Phe Tyr
                470                 475                 480

Pro Gly Ser Gly Phe Ala Phe Tyr Ser Leu Asp Tyr Met Arg Thr
                485                 490                 495

Pro Leu Asp Val Gly Thr Glu Ser Thr Trp Glu Val Glu Val Val
                500                 505                 510

Ala His Ile Arg Pro Ala Ala Asp Thr Gly Val Leu Phe Ala Leu
                515                 520                 525

Trp Ala Pro Asp Leu Arg Ala Val Pro Leu Ser Val Ala Leu Val
                530                 535                 540

Asp Tyr His Ser Thr Lys Lys Leu Lys Lys Gln Leu Val Val Leu
                545                 550                 555

Ala Val Glu His Thr Ala Leu Ala Leu Met Glu Ile Lys Val Cys
                560                 565                 570

Asp Gly Gln Glu His Val Val Thr Val Ser Leu Arg Asp Gly Glu
                575                 580                 585

Ala Thr Leu Glu Val Asp Gly Thr Arg Gly Gln Ser Glu Val Ser
                590                 595                 600

Ala Ala Gln Leu Gln Glu Arg Leu Ala Val Leu Glu Arg His Leu
                605                 610                 615

Arg Ser Pro Val Leu Thr Phe Ala Gly Gly Leu Pro Asp Val Pro
                620                 625                 630

Val Thr Ser Ala Pro Val Thr Ala Phe Tyr Arg Gly Cys Met Thr
                635                 640                 645

Leu Glu Val Asn Arg Arg Leu Leu Asp Leu Asp Glu Ala Ala Tyr
                650                 655                 660

Lys His Ser Asp Ile Thr Ala His Ser Cys Pro Pro Val Glu Pro
                665                 670                 675

Ala Ala Ala
       678

(2) INFORMATION FOR SEQ ID NO:3:

(i) SEQUENCE CHARACTERISTICS:
        (A) LENGTH: 676 amino acids
        (B) TYPE: amino acid
        (D) TOPOLOGY: linear (xi) SEQUENCE DESCRIPTION: SEQ ID NO:3:
```

-continued

```
Met Arg Val Leu Gly Gly Arg Cys Gly Ala Leu Leu Ala Cys Leu
 1               5                  10                  15

Leu Leu Val Leu Pro Val Ser Glu Ala Asn Phe Leu Ser Lys Gln
                20                  25                  30

Gln Ala Ser Gln Val Leu Val Arg Lys Arg Arg Ala Asn Ser Leu
                35                  40                  45

Leu Glu Glu Thr Lys Gln Gly Asn Leu Glu Arg Glu Cys Ile Glu
                50                  55                  60

Glu Leu Cys Asn Lys Glu Glu Ala Arg Glu Val Phe Glu Asn Asp
                65                  70                  75

Pro Glu Thr Asp Tyr Phe Tyr Pro Lys Tyr Leu Val Cys Leu Arg
                80                  85                  90

Ser Phe Gln Thr Gly Leu Phe Thr Ala Ala Arg Gln Ser Thr Asn
                95                 100                 105

Ala Tyr Pro Asp Leu Arg Ser Cys Val Asn Ala Ile Pro Asp Gln
               110                 115                 120

Cys Ser Pro Leu Pro Cys Asn Glu Asp Gly Tyr Met Ser Cys Lys
               125                 130                 135

Asp Gly Lys Ala Ser Phe Thr Cys Thr Cys Lys Pro Gly Trp Gln
               140                 145                 150

Gly Glu Lys Cys Glu Phe Asp Ile Asn Glu Cys Lys Asp Pro Ser
               155                 160                 165

Asn Ile Asn Gly Gly Cys Ser Gln Ile Cys Asp Asn Thr Pro Gly
               170                 175                 180

Ser Tyr His Cys Ser Cys Lys Asn Gly Phe Val Met Leu Ser Asn
               185                 190                 195

Lys Lys Asp Cys Lys Asp Val Asp Glu Cys Ser Leu Lys Pro Ser
               200                 205                 210

Ile Cys Gly Thr Ala Val Cys Lys Asn Ile Pro Gly Asp Phe Glu
               215                 220                 225

Cys Glu Cys Pro Glu Gly Tyr Arg Tyr Asn Leu Lys Ser Lys Ser
               230                 235                 240

Cys Glu Asp Ile Asp Glu Cys Ser Glu Asn Met Cys Ala Gln Leu
               245                 250                 255

Cys Val Asn Tyr Pro Gly Gly Tyr Thr Cys Tyr Cys Asp Gly Lys
               260                 265                 270

Lys Gly Phe Lys Leu Ala Gln Asp Gln Lys Ser Cys Glu Val Val
               275                 280                 285

Ser Val Cys Leu Pro Leu Asn Leu Asp Thr Lys Tyr Glu Leu Leu
               290                 295                 300

Tyr Leu Ala Glu Gln Phe Ala Gly Val Val Leu Tyr Leu Lys Phe
               305                 310                 315

Arg Leu Pro Glu Ile Ser Arg Phe Ser Ala Glu Phe Asp Phe Arg
               320                 325                 330

Thr Tyr Asp Ser Glu Gly Val Ile Leu Tyr Ala Glu Ser Ile Asp
               335                 340                 345

His Ser Ala Trp Leu Leu Ile Ala Leu Arg Gly Gly Lys Ile Glu
               350                 355                 360

Val Gln Leu Lys Asn Glu His Thr Ser Lys Ile Thr Thr Gly Gly
               365                 370                 375

Asp Val Ile Asn Asn Gly Leu Trp Asn Met Val Ser Val Glu Glu
               380                 385                 390
```

```
Leu Glu His Ser Ile Ser Ile Lys Ile Ala Lys Glu Ala Val Met
            395                 400                 405

Asp Ile Asn Lys Pro Gly Pro Leu Phe Lys Pro Glu Asn Gly Leu
            410                 415                 420

Leu Glu Thr Lys Val Tyr Phe Ala Gly Phe Pro Arg Lys Val Glu
            425                 430                 435

Ser Glu Leu Ile Lys Pro Ile Asn Pro Arg Leu Asp Gly Cys Ile
            440                 445                 450

Arg Ser Trp Asn Leu Met Lys Gln Gly Ala Ser Gly Ile Lys Glu
            455                 460                 465

Ile Ile Gln Glu Lys Gln Asn Lys His Cys Leu Val Thr Val Glu
            470                 475                 480

Lys Gly Ser Tyr Tyr Pro Gly Ser Gly Ile Ala Gln Phe His Ile
            485                 490                 495

Asp Tyr Asn Asn Val Ser Ser Ala Glu Gly Trp His Val Asn Val
            500                 505                 510

Thr Leu Asn Ile Arg Pro Ser Thr Gly Thr Gly Val Met Leu Ala
            515                 520                 525

Leu Val Ser Gly Asn Asn Thr Val Pro Phe Ala Val Ser Leu Val
            530                 535                 540

Asp Ser Thr Ser Glu Lys Ser Gln Asp Ile Leu Leu Ser Val Glu
            545                 550                 555

Asn Thr Val Ile Tyr Arg Ile Gln Ala Leu Ser Leu Cys Ser Asp
            560                 565                 570

Gln Gln Ser His Leu Glu Phe Arg Val Asn Arg Asn Asn Leu Glu
            575                 580                 585

Leu Ser Thr Pro Leu Lys Ile Glu Thr Ile Ser His Glu Asp Leu
            590                 595                 600

Gln Arg Gln Leu Ala Val Leu Asp Lys Ala Met Lys Ala Lys Val
            605                 610                 615

Ala Thr Tyr Leu Gly Gly Leu Pro Asp Val Pro Phe Ser Ala Thr
            620                 625                 630

Pro Val Asn Ala Phe Tyr Asn Gly Cys Met Glu Val Asn Ile Asn
            635                 640                 645

Gly Val Gln Leu Asp Leu Asp Glu Ala Ile Ser Lys His Asn Asp
            650                 655                 660

Ile Arg Ala His Ser Cys Pro Ser Val Trp Lys Lys Thr Lys Asn
            665                 670                 675

Ser
676

(2) INFORMATION FOR SEQ ID NO:4:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:4:

TCAAGACAAT GGAACCCAGG                                                 20

(2) INFORMATION FOR SEQ ID NO:5:

(i) SEQUENCE CHARACTERISTICS:
        (A) LENGTH: 36 bases
        (B) TYPE: nucleic acid
```

```
            (C) STRANDEDNESS: single
            (D) TOPOLOGY: linear (xi) SEQUENCE DESCRIPTION: SEQ ID NO:5:

CATGGAATTC GGTGACCGAT GTGCGGCTGT GAGGAG                                36

(2) INFORMATION FOR SEQ ID NO:6:

(i) SEQUENCE CHARACTERISTICS:
            (A) LENGTH: 95 bases
            (B) TYPE: nucleic acid
            (C) STRANDEDNESS: single
            (D) TOPOLOGY: linear (xi) SEQUENCE DESCRIPTION: SEQ ID NO:6:

GCAAGGGCTA CTGCCACACT CGAGCTGCGC AGATGCTAGC CTCAAGATGG                 50

CTGATCCAAA TCGATTCCGC GGCAAAGATC TTCCGGTCCT GTAGA                      95

(2) INFORMATION FOR SEQ ID NO:7:

(i) SEQUENCE CHARACTERISTICS:
            (A) LENGTH: 103 bases
            (B) TYPE: nucleic acid
            (C) STRANDEDNESS: single
            (D) TOPOLOGY: linear (xi) SEQUENCE DESCRIPTION: SEQ ID NO:7:

AGCTTCTACA GGACCGGAAG ATCTTTGCCG CGGAATCGAT TTGGATCAGC                 50

CATCTTGAGG CTAGCATCTG CGCAGCTCGA GTGTGGCAGT AGCCCTTGCT                100

GCA                                                                  103

(2) INFORMATION FOR SEQ ID NO:8:

(i) SEQUENCE CHARACTERISTICS:
            (A) LENGTH: 13 amino acids
            (B) TYPE: amino acid
            (D) TOPOLOGY: linear (xi) SEQUENCE DESCRIPTION: SEQ ID NO:8:

Xaa Gln Val Leu Ile Arg Arg Xaa Arg Ala Asn Thr Leu
 1               5                  10          13

(2) INFORMATION FOR SEQ ID NO:9:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:9:

Ala Asn Thr Leu
 1           4

(2) INFORMATION FOR SEQ ID NO:10:

(i) SEQUENCE CHARACTERISTICS:
            (A) LENGTH: 28 bases
            (B) TYPE: nucleic acid
            (C) STRANDEDNESS: single
            (D) TOPOLOGY: linear (xi) SEQUENCE DESCRIPTION: SEQ ID NO:10:

GATATCGATC CATGGCCCCT TCGCTCTC                                         28
```

(2) INFORMATION FOR SEQ ID NO:11:

(i) SEQUENCE CHARACTERISTICS:
        (A) LENGTH: 31 bases
        (B) TYPE: nucleic acid
        (C) STRANDEDNESS: single
        (D) TOPOLOGY: linear (xi) SEQUENCE DESCRIPTION: SEQ ID NO:11:

CATGGATCCT ACCGGAAGTC AAACTCAGCT A                                      31

(2) INFORMATION FOR SEQ ID NO:12:

(i) SEQUENCE CHARACTERISTICS:
        (A) LENGTH: 28 bases
        (B) TYPE: nucleic acid
        (C) STRANDEDNESS: single
        (D) TOPOLOGY: linear (xi) SEQUENCE DESCRIPTION: SEQ ID NO:12:

GATATCGATG AGTGTGAAGT CCTTGTAC                                        28

(2) INFORMATION FOR SEQ ID NO:13:

(i) SEQUENCE CHARACTERISTICS:
        (A) LENGTH: 27 bases
        (B) TYPE: nucleic acid
        (C) STRANDEDNESS: single
        (D) TOPOLOGY: linear (xi) SEQUENCE DESCRIPTION: SEQ ID NO:13:

GTCGGATCCG ACAGAGACTG AGAAGCC                                         27

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:14:

Ala Phe Gln Val Phe Glu Glu Ala
 1             5           8

(2) INFORMATION FOR SEQ ID NO:15:

(i) SEQUENCE CHARACTERISTICS:
        (A) LENGTH: 27 bases
        (B) TYPE: nucleic acid
        (C) STRANDEDNESS: single
        (D) TOPOLOGY: linear (xi) SEQUENCE DESCRIPTION: SEQ ID NO:15:

AGCTGCTCGA GGCGCTGTTG CCGGCGC                                         27

(2) INFORMATION FOR SEQ ID NO:16:

(i) SEQUENCE CHARACTERISTICS:
        (A) LENGTH: 29 bases
        (B) TYPE: nucleic acid
        (C) STRANDEDNESS: single
        (D) TOPOLOGY: linear (xi) SEQUENCE DESCRIPTION: SEQ ID NO:16:

AGCTGCTCGA GGCAAATTCT TTACTTGAA                                     29

(2) INFORMATION FOR SEQ ID NO:17:

(i) SEQUENCE CHARACTERISTICS:
             (A) LENGTH: 30 bases
             (B) TYPE: nucleic acid
             (C) STRANDEDNESS: single
             (D) TOPOLOGY: linear (xi) SEQUENCE DESCRIPTION: SEQ ID NO:17:

AGCTGCTCGA GGACCAGTGC ACGCCCAACC                                            30

(2) INFORMATION FOR SEQ ID NO:18:

(i) SEQUENCE CHARACTERISTICS:
             (A) LENGTH: 28 bases
             (B) TYPE: nucleic acid
             (C) STRANDEDNESS: single
             (D) TOPOLOGY: linear (xi) SEQUENCE DESCRIPTION: SEQ ID NO:18:

GCTGCTCGAG GACATCTTGC CGTGCGTG                                              28

(2) INFORMATION FOR SEQ ID NO:19:

(i) SEQUENCE CHARACTERISTICS:
             (A) LENGTH: 21 bases
             (B) TYPE: nucleic acid
             (C) STRANDEDNESS: single
             (D) TOPOLOGY: linear (xi) SEQUENCE DESCRIPTION: SEQ ID NO:19:

CATTCATTTA TGTCAAATTC A                                                     21

(2) INFORMATION FOR SEQ ID NO:20:

(i) SEQUENCE CHARACTERISTICS:
             (A) LENGTH: 17 bases
             (B) TYPE: nucleic acid
             (C) STRANDEDNESS: single
             (D) TOPOLOGY: linear (xi) SEQUENCE DESCRIPTION: SEQ ID NO:20:

ATGGAGATCA AGGTCTG                                                          17

(2) INFORMATION FOR SEQ ID NO:21:

(i) SEQUENCE CHARACTERISTICS:
             (A) LENGTH: 33 bases
             (B) TYPE: nucleic acid
             (C) STRANDEDNESS: single
             (D) TOPOLOGY: linear (xi) SEQUENCE DESCRIPTION: SEQ ID NO:21:

CATCTTGAGG CTAGCGGCTG CGGCGGGCTC CAC                                        33

(2) INFORMATION FOR SEQ ID NO:22:

(i) SEQUENCE CHARACTERISTICS:
             (A) LENGTH: 27 bases
             (B) TYPE: nucleic acid
             (C) STRANDEDNESS: single
             (D) TOPOLOGY: linear (xi) SEQUENCE DESCRIPTION: SEQ ID NO:22:

GTCGGTGACC GCTGCTGCGG GCTCCAC                                               27